United States Patent
Lynnworth et al.

(10) Patent No.: US 6,912,918 B1
(45) Date of Patent: Jul. 5, 2005

(54) MASS FLOW SENSOR AND METHODS OF DETERMINING MASS FLOW OF A FLUID

(75) Inventors: Lawrence C. Lynnworth, Waltham, MA (US); Christopher Smart, Framingham, MA (US); Thomas Nicholson, Whitman, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/795,980

(22) Filed: Mar. 10, 2004

(51) Int. Cl.[7] ............................................. G01F 1/66
(52) U.S. Cl. ................................................. 73/861.26
(58) Field of Search ........................ 73/861.26, 861.18, 73/861.19, 861.21, 861.22, 861.23, 861.24, 861.25, 632

(56) References Cited

U.S. PATENT DOCUMENTS

| | | | |
|---|---|---|---|
| 4,193,291 A | | 3/1980 | Lynnworth |
| 4,372,165 A | * | 2/1983 | Pitt et al. ................. 73/861.22 |
| 4,610,515 A | | 9/1986 | Tanaka |
| 4,893,496 A | | 1/1990 | Bau et al. |
| 5,515,733 A | | 5/1996 | Lynnworth |
| 6,047,602 A | | 4/2000 | Lynnworth |
| 6,094,266 A | * | 7/2000 | Trainer ........................ 356/336 |
| 6,281,973 B1 | * | 8/2001 | Trainer ........................ 356/342 |
| 2003/0089159 A1 | * | 5/2003 | Roe ........................... 73/28.04 |

OTHER PUBLICATIONS

Application for U.S. Letters Patent by Nguyen et al for Acoustic Waveguide System Dec. 23, 2003 –PAN–210J.
Lynnworth 1977 Ultrasonics Symposium Proceedings Slow Torsional Wave Sensors.
Bau et al 1993 IEEE Torsional Sensor Applications in Two–Phase Fluids.
Hiro Yamasaki et al FLOW Its Measurement and Control in Science and Industry, vol. 1, Part 2 Flow Measuring Devices, The Vortex Flowmeter pp. 975–983, 1974.
USA AMRDL–TR–75–8 Jun. 1975 Improved Ultrasonic Fuel Mass Flowmeter for Army Aircraft Engine Diagnostics.

* cited by examiner

*Primary Examiner*—Edward Lefkowitz
*Assistant Examiner*—Corey D. Mack
(74) *Attorney, Agent, or Firm*—Nixon & Vanderhye

(57) ABSTRACT

The mass flow rate sensor includes a waveguide disposed in a flow passage having a bluff body facing in an upstream direction. Waves are pulsed along the waveguide for interaction with the fluid. A receiver is coupled to the waveguide to detect a propagated wave and provides a first output signal proportional to the transit time of the propagated wave for determining fluid density. The receiver also provides a second output signal proportional to the shedding frequency of vortices from the waveguide to determine velocity. An electronics module calculates mass flow rate from the velocity times density times area of the flow passage and a constant. In other forms, the velocity is ascertained by transmitting an ultrasonic beam through the shedding vortices to determine vortex frequency which is proportional to velocity.

30 Claims, 22 Drawing Sheets

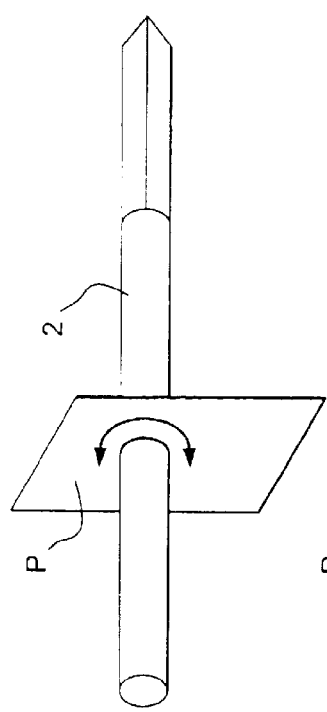
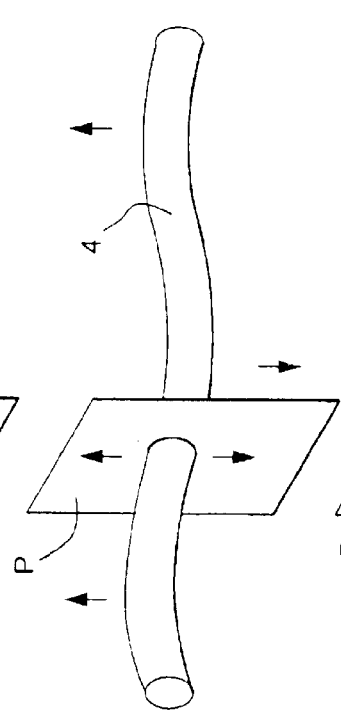
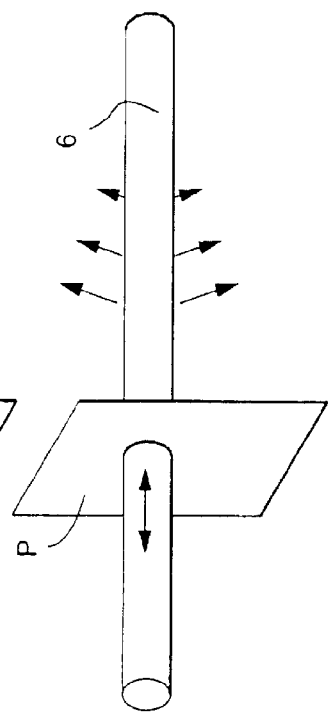
Fig. 1a
Fig. 1b
Fig. 1c

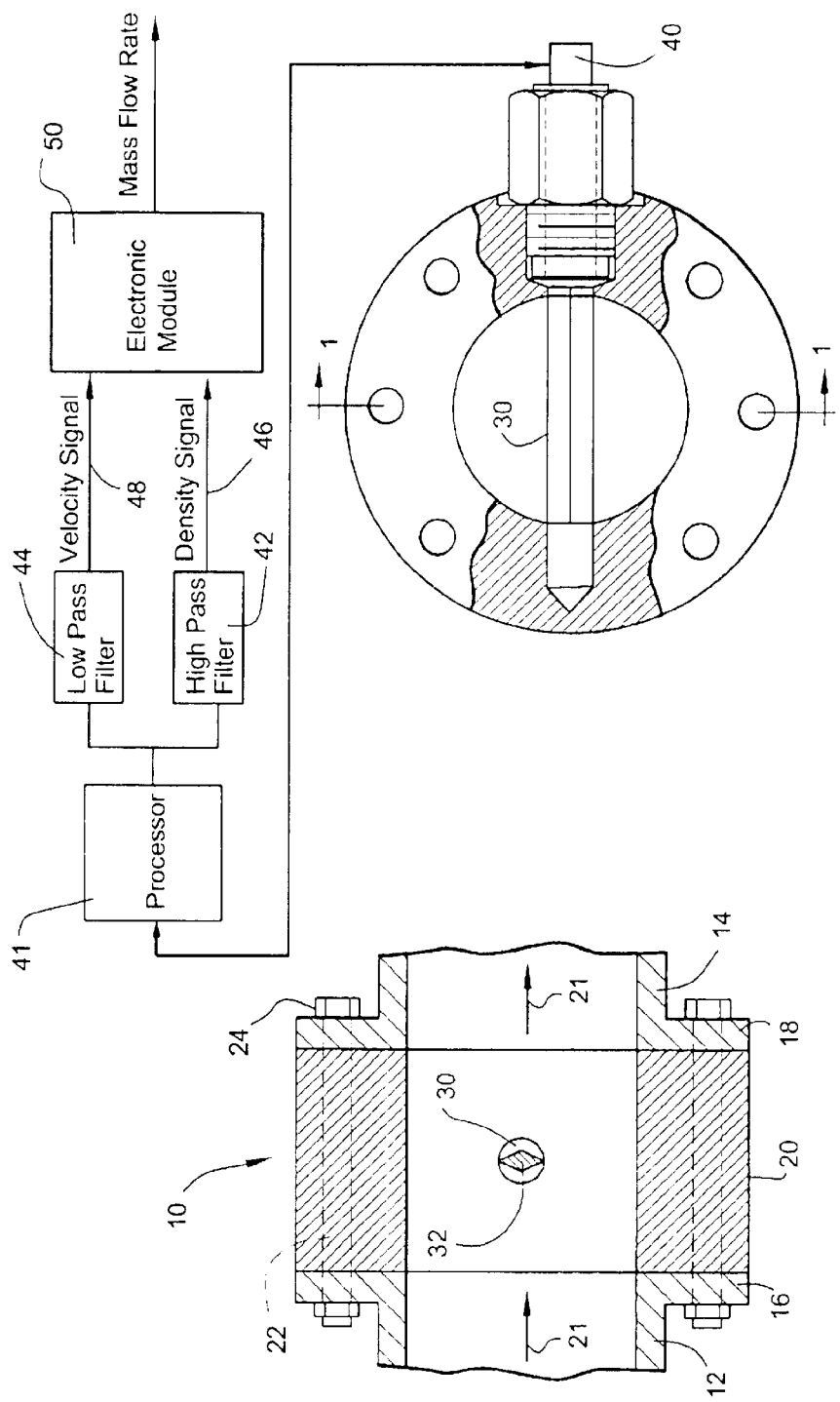

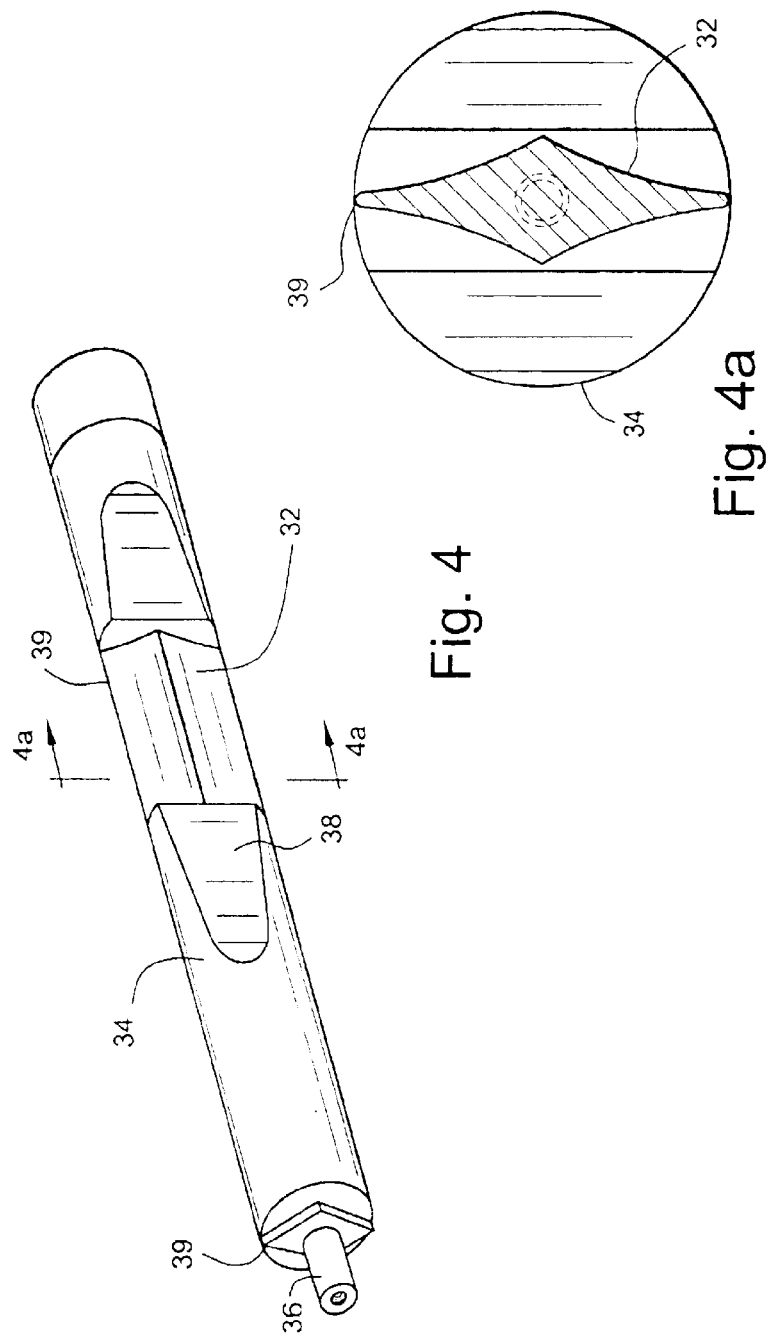

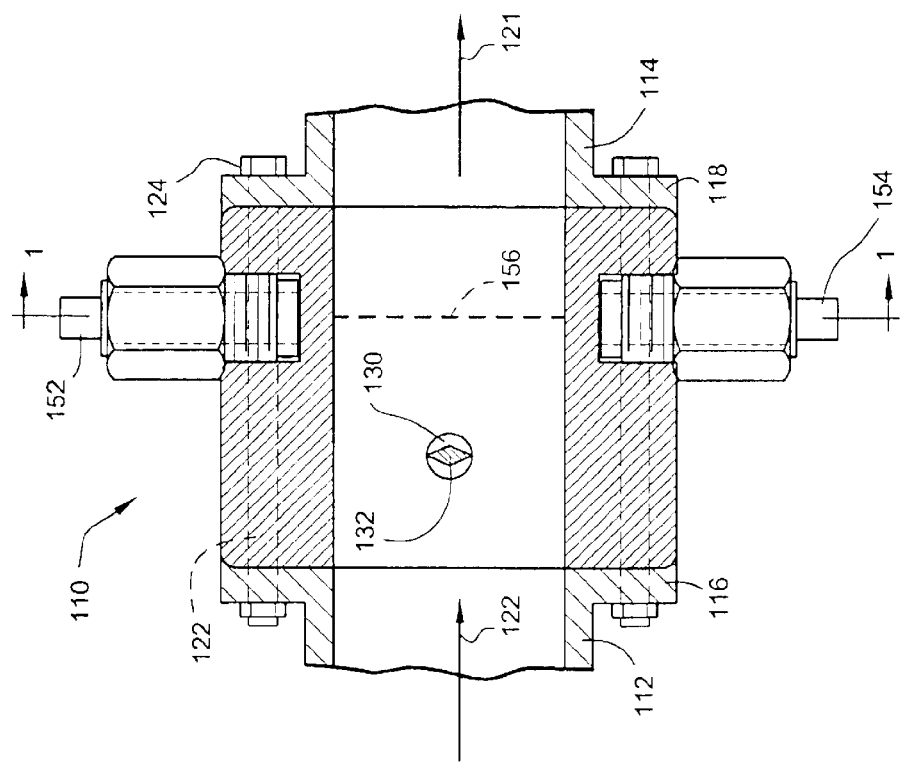

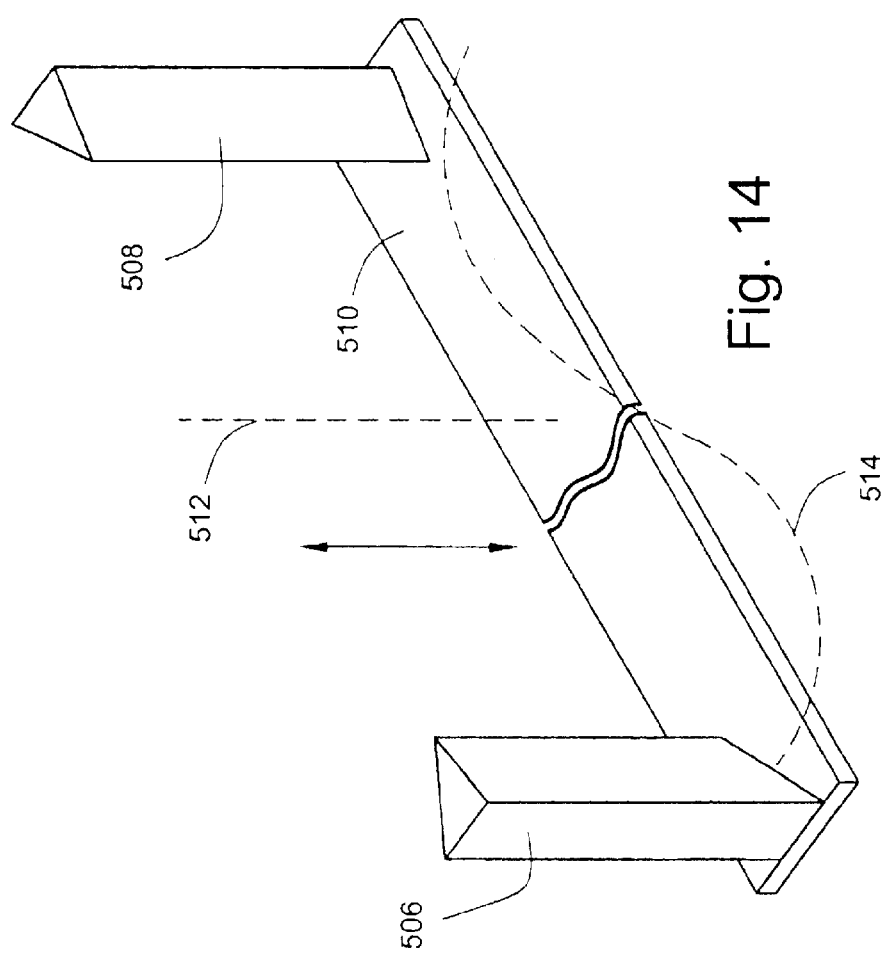

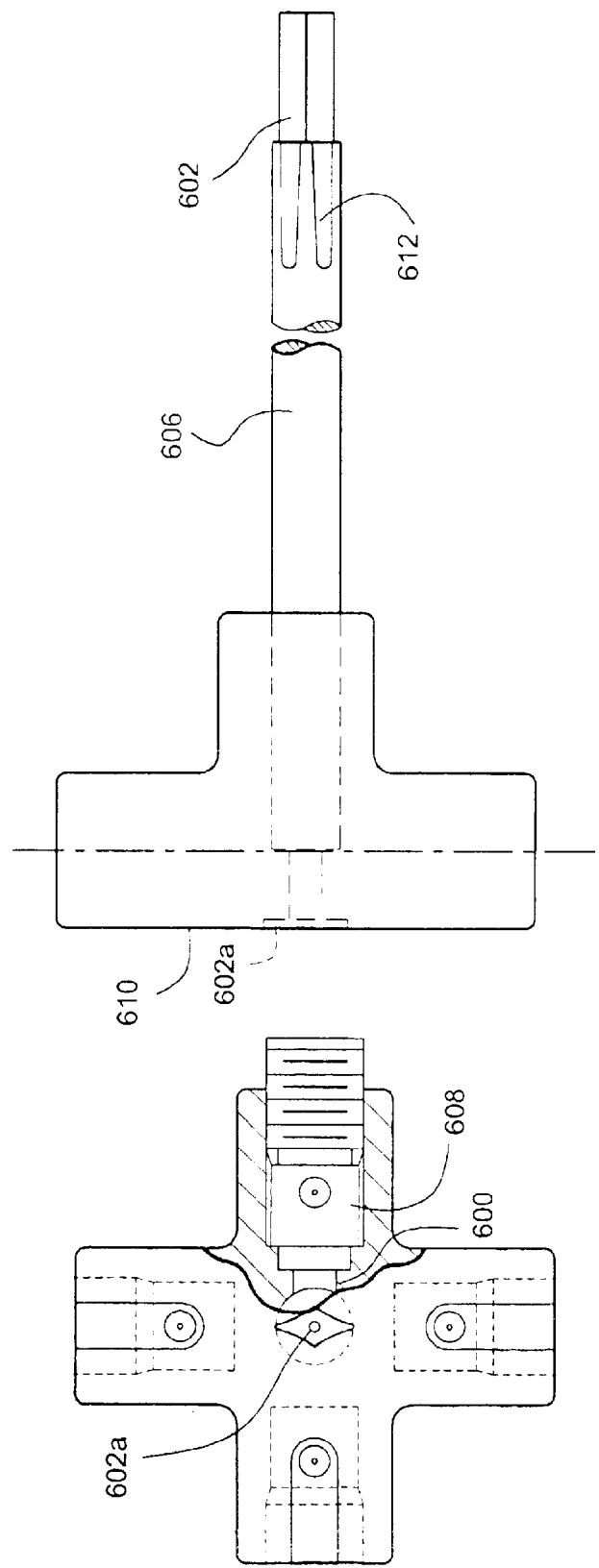

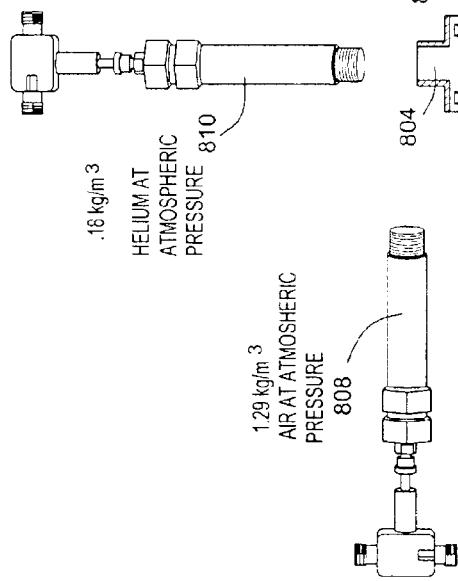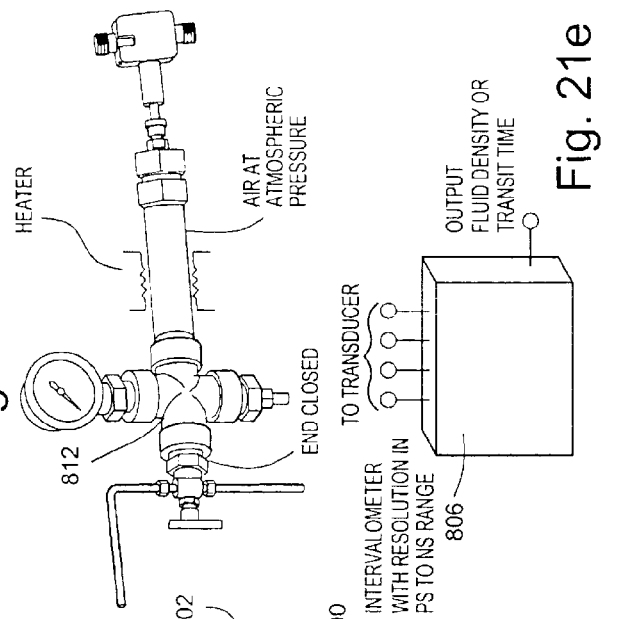

MASS FLOW SENSOR AND METHODS OF DETERMINING MASS FLOW OF A FLUID

BACKGROUND OF THE INVENTION

The present invention relates to apparatus and methods for sensing mass flow of a fluid along a flow path and particularly relates to a mass flow sensor using a bluff body in the flow path to determine fluid density and velocity and thereby the mass flow rate in a given flow passage.

In industrial process control, it is often necessary to determine the mass flow rate of fluids along flow paths, e.g. pipes. There are a number of known sensors which provide mass flow rate. For example, one sensor is based on the coriolis principle. Coriolis mass flow meters are generally considered to be highly accurate. However they do have limitations. One such limitation is that they may cause excessive pressure drop in the fluid flow, when sized smaller than adjacent piping to speed up a flow that would otherwise be too low to be readily measured. Other limitations include substantial expense for large sizes of Coriolis flow meters as well as inaccurate or erratic performance if the fluid contains entrained gases. Also not all Coriolis based mass flow meters, as well as other flow meters, can be applied in practical mounting configurations, for example, one particular measuring device generally is not usable in pipes of substantially different sizes. Nor can conventional mass flow sensors provide the accuracy, bidirectionality, ease of installation and economics necessary for a commercial mass flow sensor.

BRIEF DESCRIPTION OF THE INVENTION

In accordance with a preferred embodiment of the present invention, there is provided a mass flow sensor having a noncircular bluff body disposed in a fluid flow path for sensing density based on the transit time of a wave, preferably a pulsed, torsional wave along a waveguide in contact with the fluid and for sensing velocity based on vortices shed from the noncircular bluff body.

Ultrasonic guided waves that have a principal component of particle displacement in a plane or planes perpendicular to the density-responsive segment of the waveguide, or perpendicular to the direction of wave propagation in that segment, are slowed by a mass loading effect when the density portion of the present invention's waveguide is surrounded by a fluid of density ρ. The effect is generally much greater with liquids compared to gases, and for a given elastic material (stainless steel, titanium, aluminum, for example) the mass loading effect is usually greater for torsion compared with flexural waves, provided the waveguide segment is suitably shaped. Extensional waves propagating along waveguides, i.e., having principal motion parallel to the waveguide axis, exhibit negligible response to mass loading and therefore in most cases are not useful for determining density. On the other hand, this insensitivity to density makes extensional waves well suited for measuring the average temperature within the density segment, facilitating a compact temperature-compensated density and mass flowmeter apparatus. Torsional and flexural waves as used herein preferably propagate in their lowest order mode. By "lowest order mode" is meant one or more of the following: (a) the lowest order mode is actually launched; (b) the lowest order mode is the dominant one received even if higher order modes are launched; (c) the signal shape and/or arrival time, or propagation in the system's elastic waveguide can be adequately explained by neglecting all modes but the lowest order mode. For torsion this guarantees dispersion free propagation in straight waveguide segments of circular cross section such as the lead-in and lead-out portions. For flexural waves, the lowest order mode means at sufficiently low frequency, the wave speed in the waveguide is less than that in the adjacent fluid, avoiding radiation or leakage of energy into that fluid. Conversely, acoustic noise in the fluid, being in the longitudinal mode and generally distributed in the fluid over a wide range of frequencies, arbitrary angles of incidence, and arbitrary phases, does not efficiently or directly couple to the lowest-order flexural mode utilized in the flexural density sensor (nor directly to the lowest-order torsional mode utilized in the torsional density sensor). It is also easier to time echoes of interest if there is only one dominant mode propagating. Equivalently, in a resonance method of sensing, it is easiest to determine the resonant frequency if only one mode is dominant.

For convenience, the specification and drawings disclose electronic interrogation using a short pulse. It will be understood that the reduction of sound speed by mass loading can be measured with long pulses (tone bursts), codes, or even with continuous waves. Also for convenience, the present application refers to torsional waves for sensing density. It will be understood that in many cases, flexural waves can, for sensing density, be used, with suitable reconfiguration of the lead-in and lead-out segments, or suitable change in transducer details. In particular, application of antiparallel shear stresses to opposite sides of a waveguide launches torsional waves. Those same transducers can be used to detect bending or flexural waves if the connections to the electrical leads on one of the two transducers is reversed. Reversal of the connections can be done as often as necessary to properly sample the density and the flow. Alternatively, a second set of transducers can be coupled at the opposite end of the waveguide, with its connections appropriate at one end for torsion (pulse-echo mode) and at the opposite end for flexural mode. Still another option is to use four transducers at 90 degree intervals, two for torsion and two for flexure. Placement around the circumference would correspond to the sensor orientation, such that bending induced by shedding would be detected by the flexural receiver pair. Analogous response would be possible using piezoelectric elements bonded to the end of the waveguide, i.e., at its end face.

Sensing density based on the transit time of a torsional wave in a noncircular waveguide is based on the phenomenon that fluid acting as a mass loads the waveguide and slows the torsional wave propagating along the waveguide in proportion to the density of the fluid. A torsional wave densitometer of this type is described and illustrated in U.S. Pat. No. 4,193,291. From a later U.S. Pat. No. 4,893,496, it has been determined that a diamond-shaped cross-section is an optimal shape to measure density when the waveguide is excited in a torsional mode. Generally speaking, for accurate determination of density using a torsional waveguide, the interrogation frequencies lie in the ultrasonic range, 20-kHz and above and usually in the 20 kHz to 200-kHz range.

It will also be appreciated that fluid flow velocity is proportional to the frequency of vortices shed from a body in a flow path, provided the flow is sufficiently turbulent. That is, a properly designed bluff body sheds vortices at a frequency directly proportional to flow velocity and inversely proportional to the diameter of the bluff body. The frequency band used to measure velocity using vortex shedding however is generally less than 1,000 Hz.

In accordance with one aspect of the present invention, a noncircular bluff body waveguide disposed in a fluid flow passage is used to generate signals proportional to both flow velocity and fluid density. By using, e.g. high and low pass electronic filters and electronic processing, high and low frequency information proportional to density and velocity parameters, respectively, of the fluid may be separated from one another. That is, the velocity information contained in the low frequency (audio frequency) band and the density information contained in a high frequency ultrasonic band, e.g. 20- to 200-kHz are electronically processed. Consequently, by determining transit times of pulsed torsional or flexural waves along a waveguide proportional to density and the generated frequency or modulation frequency of continuous or pulsed waves, which modulation frequency is proportional to the vortex shedding frequency and hence velocity, and given the cross-sectional area A of the fluid flow path, and if necessary a calibration factor K, mass flow rate is obtained.

In one preferred embodiment of the present invention, a torsional waveguide generates two signals or two information packets at different frequencies which are proportional to density and velocity whereby the mass flow rate of the fluid can be determined directly from the same waveguide. In another preferred embodiment, the torsional waveguide provides a signal proportional to density. This signal is a function of the phase velocity, or transit time, in the waveguide, which in turn is a function of the density of the fluid adjacent the waveguide. A transducer generates an ultrasonic signal for transmission across the fluid flow path to a receiver to separately measure the vortex shedding frequency. Vortex shedding frequencies are measured substantially accurately in a mid range between high and low Reynolds numbers to avoid nonlinearities. As noted previously, the signals representing density and velocity are processed in conjunction with the known area of the fluid flow passage to provide the mass flow rate.

In a further preferred embodiment, the mass flow sensor senses density using a torsional waveguide. Velocity is sensed by transmitting an ultrasonic beam upstream of the waveguide across the flow path for reflection across the flow path downstream of the waveguide to a receiver. By straddling the waveguide with legs of the ultrasonic beam on respective upstream and downstream sides of the waveguide, a modulation of the downstream leg of the beam path occurs as compared with the vortex shedding measurement using the waveguide per se as in the first mentioned embodiment. A contrapropagation measurement over the reflected vee shaped ultrasonic path is thus a check on the accuracy of the velocity measurement using the waveguide and the low frequency detection of vortices shedding from the waveguide. If the waveguide exhibits point symmetry about its long axis, and is centered in line with the vertex of the vee shaped path which straddles it, a symmetrical arrangement is achieved which can measure bidirectional flow, i.e., flow approaching from either of two opposite directions. The contrapropagation method of sensing the vortex shedding frequency provides a cross check on the velocity measurement; moreover, it can extend the system measuring range down to lower Re (pipe Reynolds numbers) than where vortex shedders normally operate (i.e. below Re=10,000) and even down through transitional flow and into laminar flow where Re is less than 2000.

In a further preferred embodiment of the present invention, the vortex shedding frequency and hence velocity can be determined by the frequency of the change in sign of the circulation of the vortices. Vortices alternate from the top and bottom of the noncircular bluff body of the waveguide. By using two ultrasonic beams downstream of the waveguide each with a transmitter and a receiver and with the beams spaced axially from one another in the direction of flow, the timed differences between, in effect, clockwise and counterclockwise advancements or retardations of the beams passing through the shed vortices can be determined. For example, if the fluid passing between the beams contains a shed vortex having a clockwise circulation (rotation) and the beams are alternated clockwise and counterclockwise faster than the passage of that vortex, the transit time for the clockwise interrogation sense can be compared to the transit time for the counterclockwise interrogation sense. That is, there is a measurable difference in the transit times of the alternating clockwise and counterclockwise beam patterns. Thus, by measuring the difference in transit times around a shed vortex in the fluid of both counterclockwise and clockwise beams while a particular vortex is enclosed between the beams, the transit time in one direction will be faster than the transit time in the opposite direction. By assigning positive or negative values to this circulation, the vortex shedding frequency is detected as a change in sign from positive to negative and vice versa. The frequency of this change in sign is proportional to velocity. Because the change in sign is independent of the shape of the waveguide, provided the shape reliably sheds vortices over a reasonable range of Re (e.g. 10,000 to 100,000), one waveguide segment can be optimally shaped to provide a measurement that is accurate and responsive to density and without undue compromise to its shape to obtain the velocity measurement. The result in this preferred embodiment is an accurate measurement of both density and velocity using the same waveguide segment to provide the density and flow velocity information.

BRIEF DESCRIPTION OF THE DRAWINGS

FIGS. 1a, 1b and 1c are schematic general representations of waveguides subjected to torsional, flexural and extensional waves, respectively;

FIG. 2 is a fragmentary axial cross section view of a sensor in a pipe according to a preferred embodiment of the present invention;

FIG. 3 is an axial end view of the sensor with parts broken out and in cross section and a schematic illustration of electronic circuitry;

FIG. 4 is a perspective view of a sensor element;

FIG. 4a is a cross-sectional view of the waveguide illustrating rounded edges of the diamond shaped waveguide taken about line 4a—4a in FIG. 4;

FIG. 6 is a view similar to FIG. 2 illustrating another embodiment hereof;

FIG. 14 is a fragmentary perspective view of the sensor of FIG. 13 with parts broken out for ease of illustration;

FIGS. 15 and 16 are respective axial and side elevational view of a further form of a waveguide;

FIGS. 21*a*–21*e* illustrate apparatus for high-resolution steady state and transient calibration in air or inert gases at rest for torsional waveguide density sensors whose subsequent preferred density and mass flowrate application typically will be in flowing liquids.

DETAILED DESCRIPTION OF THE INVENTION

In FIG. 1*a* there is illustrated a waveguide 2 which may be excitable in a torsional mode. As illustrated, the principal motion in the waveguide is a vibratory torsional motion in a plane P perpendicular to the long axis of the waveguide. As the torsional wave in waveguide 2 passes the plane P, if it is a lowest order torsional wave, all elements in waveguide 2 that are in that plane rotate either clockwise or counterclockwise about the axis of the waveguide, much like solid body rotation, but on a microscopic scale. In FIG. 1*a*, a diamond shaped segment of the waveguide noted in the following description is illustrated. Torsional waves propagating along the noncircular diamond portion of the waveguide of FIG. 1*a* are slowed by a mass loading effect when immersed in a fluid at rest or flowing. The flow may be directed, for example, in a direction perpendicular to the long axis of the waveguide. In FIG. 1*b*, there is illustrated a waveguide 4 in which the lowest order flexural waves are introduced similarly having a principal motion in a plane P perpendicular to the axis of the waveguide. When the waveguide 4 is immersed in a fluid, the waves are slowed by the mass loading effect. In FIG. 1*c*, a waveguide 6 is provided with extensional waves. Extensional waves have a principal motion parallel to the long axis of the waveguide and the mass loading effect in a fluid is negligible. For both torsional and flexural waveguides of the present designs, there is negligible radiation into the flowing fluid whereas in the extensional waveguide the wave energy radiates into the surrounding fluid. The lowest order mode eliminates or keeps small, dispersion for torsion; and it allows an antisymmetric flexural wave to propagate at a phase velocity in its wave guide low enough so there is no significant radiation of compressional waves into the adjacent fluid, provided the flexural frequency times the waveguide diameter or thickness is sufficiently small. For these reasons, lowest order modes are preferred. Unless otherwise specified herein, and although a torsional waveguide is used as a representative example, the guided waves responsive to density may be considered torsional or flexural according to the particular sensor's design.

Figure 1D:
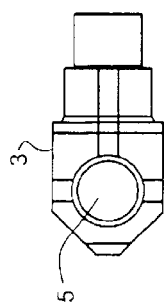
FIGS. 1d–1h are schematics of these waveguides showing specific details of exciting, securing, impedance matching, shielding, curving, and supporting without introducing spurious echoes.
Figure 1E:
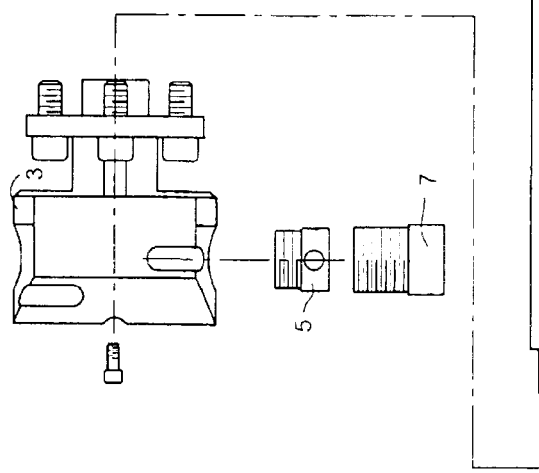
Figure 1F:
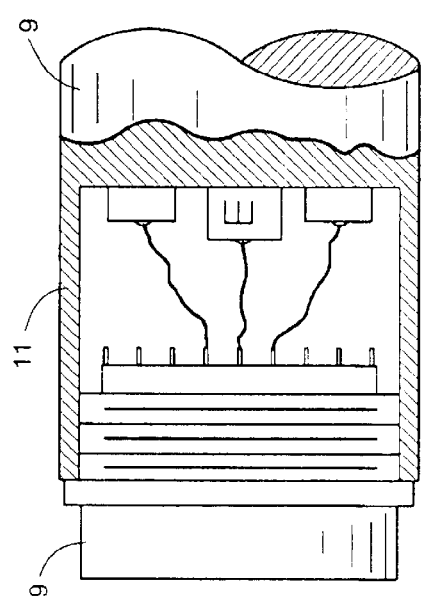
Figure 1G:
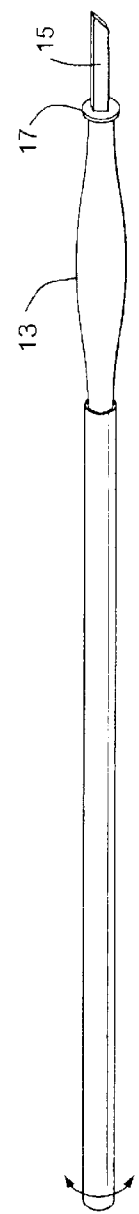
Figure 1H:
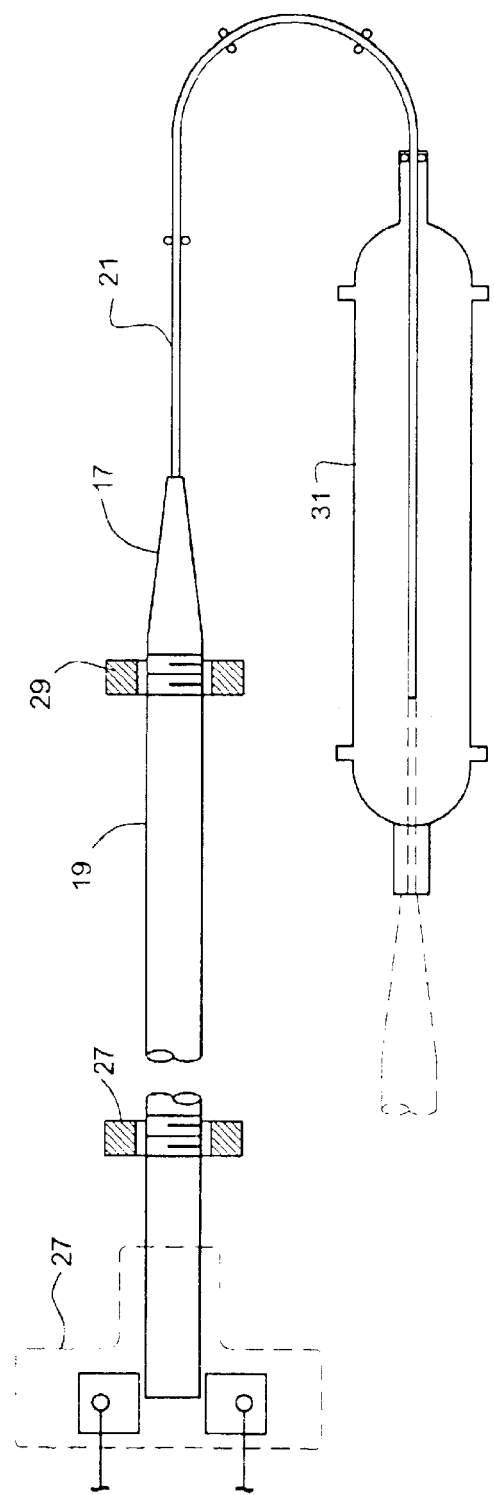

The ultrasonic literature provides examples of magnetostrictive and piezoelectric means for generating and detecting one or more of the modes of interest here. But these known methods are not necessarily optimum for accomplishing these objectives in a compact manner nor for doing so with waveguides of diameter sufficiently robust for application in flowing gases, steam or liquids. The group of FIGS. 1*d*–1*h* shows details appropriate to optimizing the sensor system for the present purposes. FIG. 1*d* illustrates a top view of the clamp 3 of FIG. 1*a* in which opposed pairs of commercially available shear transducers 5 can be pressure coupled to provide shear stress parallel, perpendicular or at 45 degrees to the waveguide axis, as projected in the top view. FIG. 1*e* shows the clamp 3 in side elevation, with one transducer and its associated clamping screw 7 drawn partly exploded. In some situations a more compact transducer assembly is achieved by bonding piezoelectric segments of shear or extensional (E) mode directly on the end face or in an end cavity of the waveguide 9 which, in FIG. 1*e* is enclosed within a sheath 11. FIG. 1*f* shows a multipin electrical connector 9 threaded into a thin-walled extension 11 of the waveguide, where the wall thickness w<<D where D is the waveguide diameter. Further details are given later in connection with FIGS. 17*a*–*d*. While the waveguide 9 shown in FIG. 1*e* has one zone at the far right, the torsional energy can be partitioned, as shown in FIG. 1*g*, into two series-connected zones 13 and 15 by employing a pair of conical impedance transformers oppositely-tapered. A thin disk 17, i.e. thin compared to torsional wavelength, separates the two zones. Zone 13 is circular in cross section and senses temperature. The diamond zone 15 senses density and requires temperature compensation. In the preferred lowest-order torsional mode the wavelength is large compared to waveguide diameter and this allows shallow engraving of material identifier (e.g. 6061 aluminum) or function (e.g. temperature) without introducing spurious echoes. FIG. 1*h* shows a conical impedance transformer 17 reducing the diameter of the waveguide 19 down to a size that is flexible sufficiently to be curved through an arc of 180 degrees. The reduced size is indicated at 21. The larger diameter portion of the waveguide is connected to the clamp 27 which contains the transducers is locally threaded e.g. at 23 or locally deformed into, for example, an elliptical bump, to facilitate reflectionless mechanical engagement by a two-piece threaded collar. One collar 25 secures the waveguide 19 to the clamp 27 and the other collar 29 secures the waveguide to a vessel 31 in which fluid flows. The collars, properly secured to a pipe, can resist axial movement that might otherwise occur during removal of the sensor from a pressurized pipeline, yet without generating spurious echoes in normal operation. A small tapped hole at the remote end of the waveguide can be centralized in a sheath by means of a small screw and washer (not shown). The remote end of the waveguide is of course supported e.g., by suitable seals at the remote end of vessel 31. The operation of the waveguide 19 is the same as the operation of the waveguide as set forth in various embodiments herein.

Referring now to the drawings particularly to FIGS. 2–4, there is illustrated a mass flow rate sensor, generally designated 10, according to an aspect of the present invention. Sensor 10 is designed for interposition within a fluid flow path to measure with associated electronics the mass flow rate of the fluid flowing through the flow path. While the flow path may be of any configuration, e.g., a flow path internal to a machine, the present invention is illustrated with respect to a sensor 10 interposed in a pipe defining a fluid flow path. Thus, as illustrated in FIG. 1, two pipe sections 12 and 14 for flowing fluid are provided with end flanges 16 and 18, respectively, spaced from one another to enable insertion of the sensor 10 in the form of a wafer or spool 20. The wafer or spool 20 is preferably annular in configuration having a flow path corresponding in diameter to the flow path through pipes 12 and 14. Bolt hole openings 22 are provided through the wafer or spool 20 for alignment with corresponding openings through flanges 16 and 18 whereby through bolts 24 secure the pipes to one another with the wafer or spool 20 of the sensor 10 disposed between the pipe flanges. The direction of the fluid flow is indicated by the arrows 21. The wafer body may be manufactured with its OD (outside diameter) matching a circle that just fits inside the flange bolt pattern. Alternatively, it may be slightly larger and notched with arcs having radii matching the bolt radii, to fit the bolt pattern, thereby controlling its rotational orientation.

In this first aspect of a mass flow meter illustrated in FIGS. 2–4, a single waveguide is used to ascertain both density $\rho$ and flow velocity V. It will be appreciated that mass flow rate M is determined by the formula $M=KA\rho V$ where $\rho$ is the density of the fluid, V is the fluid velocity, A is the area of the flow passage through the sensor and K is a factor that is close to unity over a wide range of turbulent flows. In this embodiment, density $\rho$ is determined by the transit time of a pulsed wave, preferably a torsional wave, in a waveguide 30 disposed in the fluid flow path and wetted by the fluid. Flow velocity V is proportional to the frequency of vortices shed from the waveguide and the frequency of response of the shedding vortices is determined using the same waveguide 30 used to determine the density $\rho$. The waveguide 30 is preferably disposed diametrically across the flow path. As explained previously, depending on the shape of the vortex shedder, transducer type and connections, the shedding may be detected in a passive mode responsive to torsional or flexural waves. For simplicity, seal details in FIGS. 3 and 18, and other drawings are omitted where a transducer assembly or waveguide penetrates a pressure boundary. It will be understood that the seals may include known O-ring seals, gasket seals, tapered pipe thread seals, compression seals, epoxy seals, etc.

Referring to FIG. 4, the waveguide 30 may comprise a solid rod or tube which spans between opposite sides of the flow path in the wafer 20. As noted in the prior U.S. Pat. No. 4,893,496, a section 32 of the waveguide 30 may be formed of a diamond shape having an aspect ratio of about 3 to 1 and which spans the flow path. It has previously been determined that the diamond shape in a torsional waveguide provides optimum accurate results for the determination of the density parameter. The diamond shape of the torsional waveguide sensor also serves as a vortex shedder in the flow stream. As noted below, shapes other than diamond shapes may be used to optimize the density and velocity measurements for a given single waveguide. The distal end of the waveguide 30 includes a generally cylindrical lead-in 34 terminating in a reduced diameter security hub 36. The lead-in 34 has a short section 38 forming a short impedance match which tapers in a direction toward the diamond-shaped section 32. The security hub 36 enables the waveguide 30 to be secured at one end within the wafer 20. The hub 36 is illustrated as cylindrical but may be noncircular, e.g., square, rectangular, elliptical or oval so that when fully engaged in a corresponding cavity within the wafer, the waveguide 30 cannot rotate. Secured in this way, the waveguide resists pushing, pulling or twisting relative to the enclosure that houses the transducers. Because the security hub 36 must be of a diameter having a polar moment of inertia small compared to the cylindrical waveguide, it is structurally relatively weak. To prevent over-torquing of the hub, there is provided a short axial projection 39 that mimics the noncircular pattern of the sensor section 32, i.e., the diamond cross section. This projection 39 is large enough in cross section to withstand torquing and yet is sufficiently short, to not materially degrade the wave pulse e.g. a torsional guided wave pulse. Also it provides an unambiguous method of visually verifying the orientation of the diamond-shaped sensor 32 vis-à-vis the flow path. That pattern may be mimicked on the external surface of the clamp, e.g. an engraved pattern surrounding the security screw that threads into hub 36.

The opposite end of the sensor 30 includes a transducer 40 (FIG. 3) attached to the waveguide sensor 30 which excites the waveguide preferably in a torsional mode, although excitation may be in a flexural mode or in both flexural and torsional modes. The transducer 40 and waveguide 30 are secured in a tapped opening in the wafer.

It will be appreciated that the transducer 40 under control of an electronic processor 41 generates pulses for transmission along the waveguide 30, and in this nonresonant embodiment, receives echo informational packets. Transducer 40 generates a signal, i.e. an echo pattern responsive to the pulse-echo transit time of the wave, preferably a torsional wave, excited in the waveguide and returned. That signal includes a transit time t corresponding to one or more traverses of the density-responsive sensor segment, from which, after subtraction of a reference time (such as the transit time for the sensor in vacuum) and after compensation for temperature effects, may be extracted an increment of transit time $\Delta t$ proportional in a high frequency ultrasonic range to the fluid density $\rho$ and in a low frequency range to the fluid flow velocity, the velocity being proportional to the vortex shedding frequency. Consequently, the signal from the transducer 40 may be processed through high and low pass filters 42 and 44, respectively, in the processor 41 to provide signals 46 and 48 respectively proportional to density and velocity. These signals may be further processed in an electronics module 50 or in the processor 41 to ascertain the mass flow rate for a given area of flow path. The electronics may comprise a processor 41 as illustrated or a logic array or ASICS. The implementation of the electronics may be in the form of a computer readable medium with executable instructions. If the waveguide twists in reaction to the shedding, then the torsional echoes may be modulated by that reaction twist, that modulation having a fundamental frequency proportional to the flow velocity. If the waveguide bends rather than twists in reaction to the shedding, then one of the torsional-generating transducers may detect the bending as a low frequency flexural mode.

It will be appreciated that the noncircular cross section of the waveguide, and particularly the diamond-shaped section 32 of the waveguide provides accurate results for determining density when the waveguide is excited in a torsional mode. For brevity, the term diamond shape includes a shape with flat faces as well as with curved faces associated with a cusped diamond. Vortices are shed alternately off opposite edges of the diamond-shaped section 32 and afford a modality for measuring flow velocity as a function of the frequency of those vortices. The diamond shape section 32, which is optimal for determining density, and while enabling vortex shedding, may have a different cross-sectional configuration to provide an optimum compromise between ascertaining density using a torsional waveguide and ascertaining velocity by measuring the vortex shedding frequency. As a simple example, for sensing density only, which can be accomplished in a fluid at rest or at low velocity, there would be little wear and all edges of the diamond could be manufactured as sharp edges. However, for use in flowing streams, where the sharp edges are subject to wear, and recognizing that the distance between the sharpest edges must be known accurately in order to use this shape as a vortex shedder, the present invention also includes a slightly-rounded or radiused pair of opposed edges 39 (FIG. 4a). In one numerical example, the edges 39 may be rounded to D/100 where D=waveguide diameter.

For an elastic waveguide of thickness or diameter in the approximate range 0.5 to 2 cm, when interrogated with a lowest-order torsional mode, the density-responsive segment and adjacent regions are characterized as follows: transformer normalized length dimension is π times the waveguide diameter D, in conjunction with a diamond or cusped diamond density sensing segment having a major diameter D and a minor thickness D/π. If used with a two-bladed transformer, then the blade at its thinnest region has a thickness of D/e where e is the base of natural logarithms. If radiused to preserve a relatively sharp edge, then said radius should be about D/100 . If fillet-radiused where the diamond or cusped diamond intersects the lead-in or lead-out portions, to avoid stress concentration, then the radius shall be on the order of D/10 to D/100. If a cusped diamond rather than flat diamond is used, the radius of the cusp should be on the order of D and preferably D exactly. Note that if the waveguide diameter D=0.318 inches (8.1 mm) or about 5/16 inches, the length of the taper according to the above guideline is 0.318π=1 inch (25.4 mm). This is a measure of the compactness achievable in the impedance matching portion, and is conducive to achieving an overall sensor compactness. A two-sided taper this short has been found effective as a reflectionless torsional matcher even with D as large as 19 mm. The torsional speed in the tapered matcher slows from where it intersects the round end to its nearly-rectangular end. The matcher, being noncircular, responds to the density of the adjacent fluid. This characteristic can be utilized in flowmetering where the pipe is not full, to sense liquid level and verify that the torsional density sensor is fully immersed, provided the waveguide is installed vertically. It is usually preferred to use both of the tapers to match impedances where the objective is to increase the transmission coefficient across the boundary. This means, to match from a round cross section to diamond, two tapers will exist and preferably be symmetrically disposed on each side of the waveguide axis. However, it is possible to match impedances in other ways, e.g., use just one taper to partly overcome the mismatch at a boundary such as between a waveguide's round lead-in and a diamond sensor segment. In the one-taper (one-bevel) case, the transformation of acoustic impedance occurs because of the influence of one plane surface, namely, the taper on one side of the waveguide. Transformation may not be as complete with one taper compared to two, for a given set of geometrical and waveguide material constraints. It may be mentioned that the taper can be non-planar (i.e., it can be curved) and can intersect the outer surface of the waveguide's round cross section smoothly (gentle blend) or abruptly depending on whether an echo is desired or not desired from that intersection.

Consequently a number of different shapes have been ascertained which, according to application details and manufacturing constraints, provide useful and potentially optimum shapes for determining both density and velocity. For example, those shapes have been determined to generally comprise bluff noncircular bodies. Again, density may be sensed in a waveguide of circular cross section if the interrogating wave is flexural, whereas if torsion is used then the cross section must be noncircular. While a common example of a vortex shedding shape is a flagpole, i.e., a cylinder of circular cross section, industrial vortex shedders usually are of a noncircular shape. In FIGS. 5a–5i, there are illustrated a number of different cross-sectional shapes for the waveguide sensor section 32 which enable measurements at different frequencies to optimally determine both density and velocity using the same waveguide sensor segment to sense both parameters. In some cases an extensional wave interrogates the same sensor segment. The transit time of the extensional wave typically increases in a known or calibratable manner as temperature increases, and in that case the temperature is the third parameter sensed in the same segment. However, as the shedder must be sufficiently rugged to withstand flow, its mass may have a thermal response time on the order of seconds. "Optimizing" a sensor requires consideration of all key parameters that must be measured, along with material and other constraints. In many situations, liquid temperature and density vary slowly but flow can vary rapidly. System design takes into account the different response times required for the measurands of interest, basically their steady state values, but including, optionally, transient responses. Means for determining steady state and transient response are described later in connection with FIGS. 21a–21e.

Figure 5A:
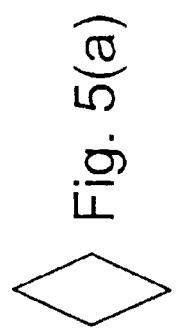
FIGS. 5(a)–5(i) are cross sections of various forms of the sensor.
Figure 5B:
Figure 5C:
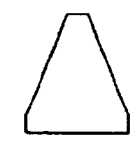
Figure 5D:
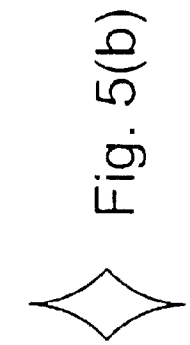
Figure 5E:
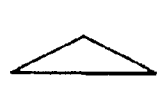
Figure 5F:
Figure 5G:
Figure 5H:
Figure 5I:

The sensor section cross sections 32 are illustrated in FIGS. 5(a)–5(i) with the flow direction being from left to right in the various drawing figures. In FIG. 5(a), there is illustrated a diamond cross-sectional shape with an aspect ratio of about 3. In FIG. 5(b), the sides of the diamond shape are cusped. In FIG. 5(c), an equilateral triangle is provided with one flat face normal to the direction of fluid flow. In FIG. 5(d), the sides of the equilateral triangle are cusped. In FIG. 5(e), there is illustrated a half-diamond shape having an aspect ratio of about 6 with its leading face forming the bluff face normal to the flow direction. FIG. 5(f) illustrates a half-diamond shape with an aspect ratio of less than 1 and the smallest face forming the bluff face normal to the fluid flow direction. FIG. 5(g) represents a polygonal shape close to that of a triangle with the upstream corners of the triangle flattened and the downstream apex flattened in a direction normal to the flow direction. FIG. 5(h) represents a rectilinear, e.g. square, waveguide. Finally, FIG. 5(i) is a teardrop shaped waveguide with the arcuate face facing upstream. These various cross-sectional configurations of the waveguide provide a compromise between cross-sectional shapes which optimize the density-velocity parameters using the respective torsional waveguide and vortex shedding measuring systems so that a single waveguide may provide accurate reliable sensing of both density and velocity to produce an accurate mass flow meter. Shapes having point symmetry about their major axis, such as FIGS. 5(a, b, h) shed the same whether flow is from the left or right, and so would be preferred if flow is bidirectional. Shapes like the teardrop (FIG. 5i) would be expected to yield larger reactive torque when vortices shed, compared to a square cross sectional shape. Torsional transducers, operating in a listening or passive mode, are appropriate for detecting the frequency of the alternating torque. Conversely, the square or round cross section would be expected to yield bending or flexural signals at the vortex shedding frequency. Thus the optimum shape includes consideration of the transducer and electrical connections and signal processing. Depending on ambient noise, vibration, cavitation or impact noise from particulates, the waveguide listening mode may or may not suffice to achieve the desired accuracy in flow velocity measurement. In simple terms, if the environment is too noisy, it may be necessary to utilize higher frequency active ultrasonic interrogation methods in the wake, to get away from the noise interference which contains significant energy at the same frequency that vortices are shed from the waveguide.

Figure 7:
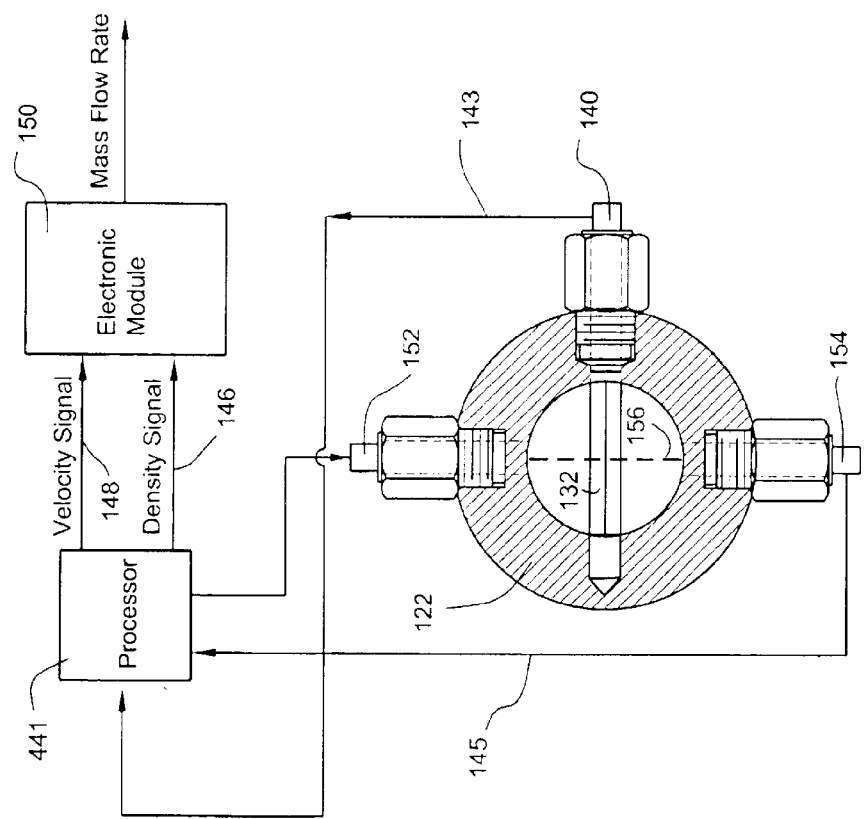
FIG. 7 is a schematic cross sectional view thereof with associated electronics.

Referring to FIGS. 6 and 7, wherein like reference numerals are applied to like parts as in the prior embodiment preceded by the numeral "1", there is illustrated a mass flow meter 110 according to another aspect of the present invention. In this aspect the waveguide 130 has a cross section optimized for determining density, i.e., a diamond cross section 132. In this aspect, the signal 143 from the transducer 140 on the waveguide 130 contains intervals related uniquely to density. (This assumes temperature compensation and calibration.) Two additional transducers 152 and 154 are provided downstream of the waveguide 130 in the region of the flow path containing vortices shed from the waveguide sensor section 132. Transducers 152 and 154 serve as an exciter and receiver for generating a sound beam 156 across the flow path and receiving the beam, respectively. It will be appreciated that absent vortex shedding, a steady signal is received by the receiver 154 from the exciter 152. However, once the beam 156 encounters vortices downstream of the waveguide sensor 130 and in the flow path a modulation of the phase and/or amplitude of the signal received by the receiver 154 is obtained. The modulation frequency within the modulated signal 145 (FIG. 7) from receiver 154 is thus proportional to the vortex shedding frequency and is electronically processed by processor 141. By processing the signal 143 from the torsional waveguide sensor 130 and the vortex shedding signal 145 derived from the interrogating sound beam 156 downstream of the waveguide sensor, the density and velocity parameters can be ascertained. Given the area of the flow passage, the electronics module 150 may therefore provide a measurement of the mass flow. It will be understood that the transducers placed downstream may be on opposite sides of the pipe as shown; they may, however, be oriented to interrogate at an angle other than 90 degrees to the pipe axis;

One or both transducers may be wetted to increase the signal to noise ratio. If the fluid is a gas they may be wetted and isolated acoustically by means illustrated in U.S. Pat. No. 5,515,733, issued May 14, 1996. If both are clamp-on and the fluid is a gas, the transducers may be positioned similar to those shown in U.S. Pat. No. 6,626,049, issued Sep. 30, 2003, but with axial spacing not so large as to straddle two shed vortices.

Figure 8:
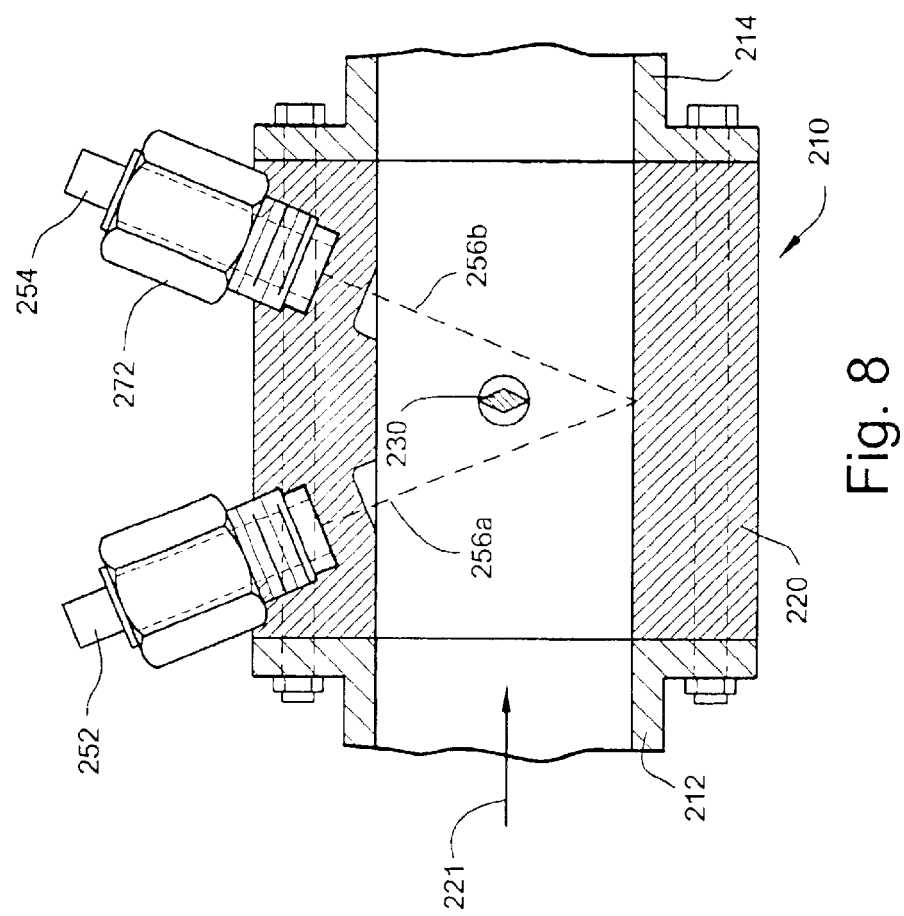
FIG. 8 is a view similar to FIG. 2 illustrating a further embodiment hereof.
Figure 9:
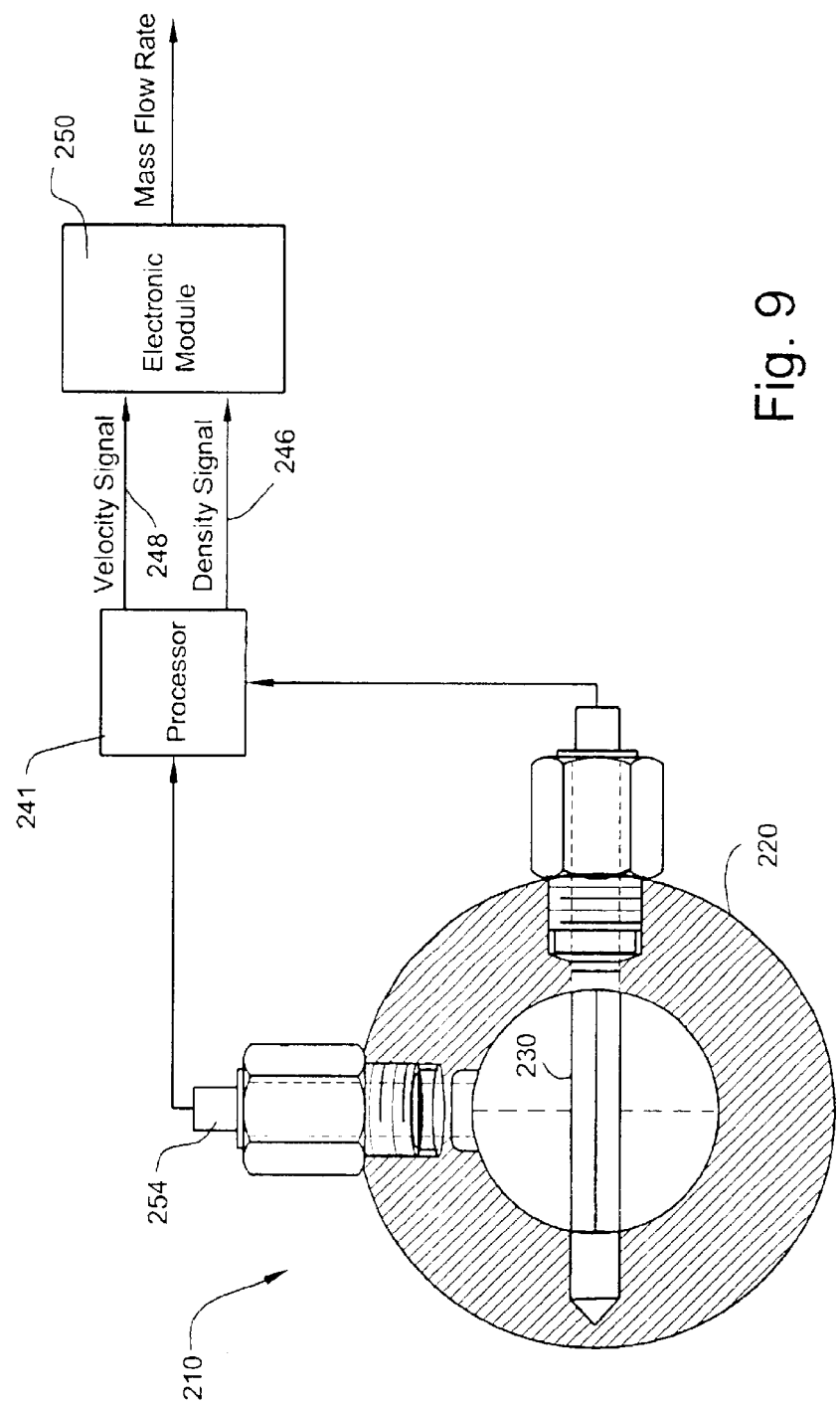
FIG. 9 is a schematic axial view of the sensor of FIG. 8 with associated electronics.

Referring to FIGS. 8 and 9, there is illustrated a further aspect of the present invention wherein like parts as in prior embodiments are denoted by like reference numerals preceded by the numeral "2". The sensor 210 includes transducers 252 and 254, i.e. an exciter and a receiver which lie on opposite axial sides of the waveguide sensor 230. In this form the torsional waveguide sensor 230 provides signals uniquely related to density and velocity as in FIGS. 2 and 3 utilizing the preferred diamond-shaped waveguide. The exciter 252, however, provides a sound beam 256 which straddles the waveguide and is detected by receiver 254. For example, the exciter 252 transmits a sound beam 256 across the fluid flow path in a first leg 256a thereof at a location axially upstream of the waveguide sensor. The sound beam bounces off the opposite wall of the wafer 220 for return along a second leg 256b downstream of the waveguide 230 for reception by the transducer. As a result of this configuration, there will be a modulation of the phase and/or amplitude introduced as the ultrasonic wave traverses the downstream leg 256b of the sound beam 256. The fundamental frequency of this modulation equals the vortex shedding frequency. The processor 241 receives the velocity and density signals 248 and 246 respectively, and which signals are combined in electronics module 250 to provide the mass flow rate. The vee path over which modulation is sensed, can also be interrogated in the contrapropagation manner, providing a cross check as well as extending the flow range to regions of Reynolds numbers Re where vortex shedding is unreliable, namely, below Re=10,000 and down to the transitional region (Re=2000 to 4000) and even into the laminar region where Re<2000. The vee path contrapropagation method can respond as fast as one ms to flow transients that are brief compared to the period of the vortex shedding, or short compared to the thermal response time of the shedder.

It will be appreciated that in this embodiment two measurements of the vortex shedding frequency may be obtained; one from the waveguide sensor 230 in accordance with the embodiment illustrated in FIGS. 2–3 and a second measurement from the ultrasonic beam 256 straddling the waveguide sensor and measuring vortex shedding frequency. Each measurement serves as a check on the accuracy of the other measurement. For use in the mass flowrate computation, the parameter having minimum standard deviation may be preferred.

Figure 10:
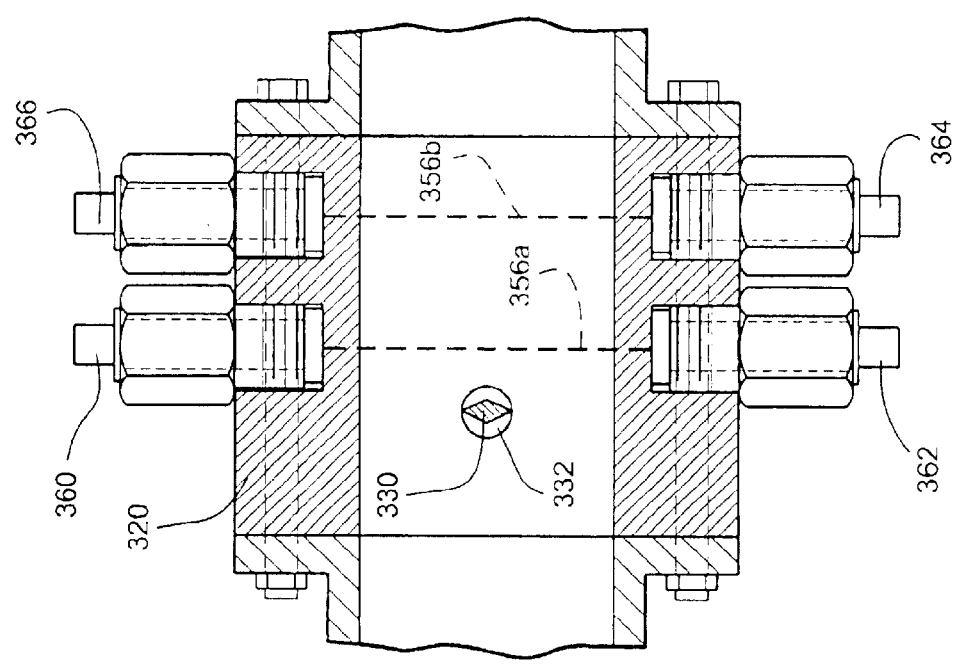
FIG. 10 is a view similar to FIG. 1 illustrating a still further embodiment hereof.
Figure 11:
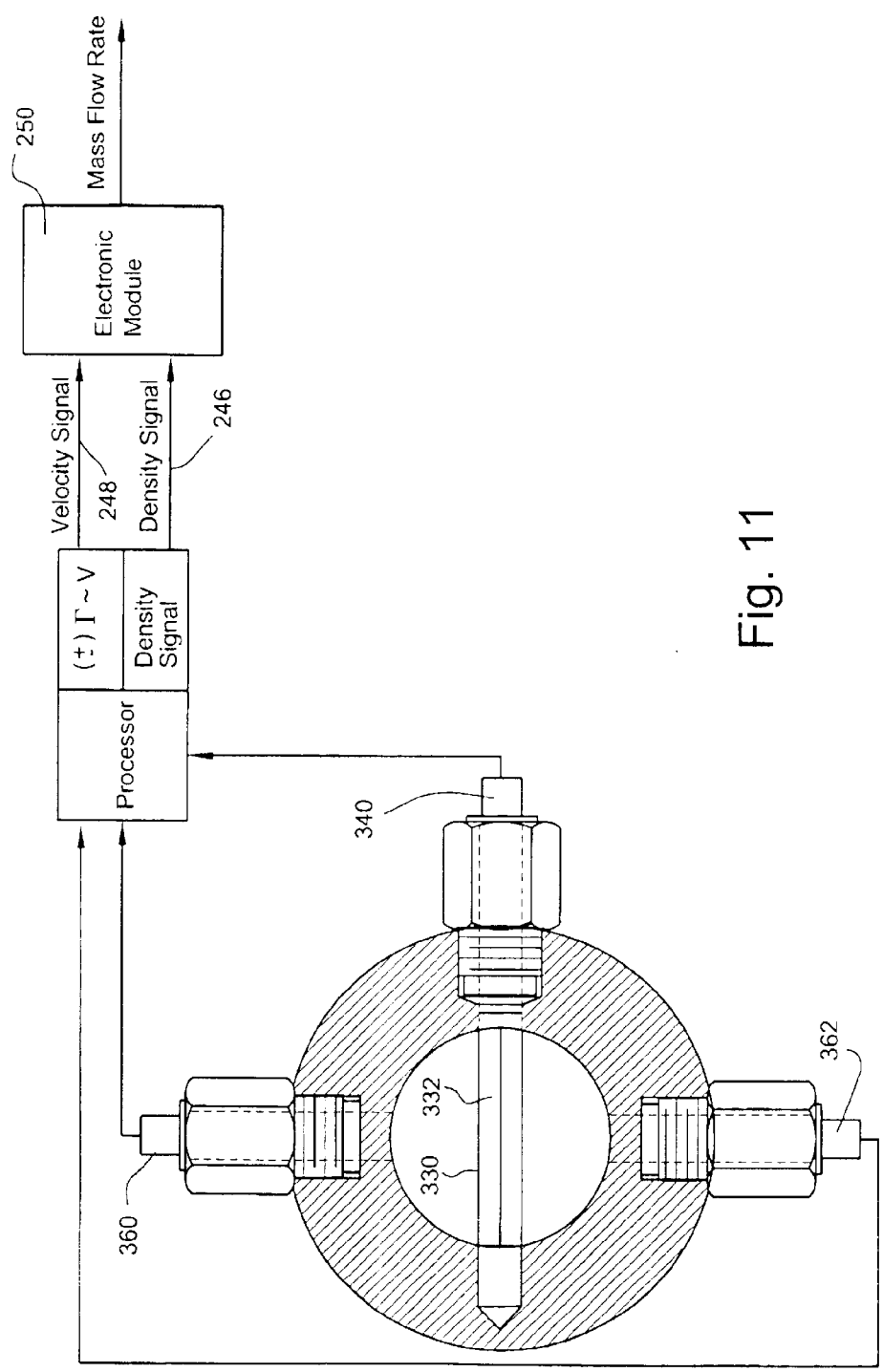
FIG. 11 is a schematic illustration of FIG. 10 with associated electronics.

Referring now to the embodiment of FIGS. 10 and 11, wherein like reference numerals are applied to like parts as in prior embodiments preceded by the numeral "3", there is illustrated a waveguide 330 in a wafer 320 similar to the embodiment of FIG. 2. In this embodiment, two ultrasonic beams 356a and 356b are provided at axially spaced positions one from the other downstream of the waveguide 330. (They could also be positioned to straddle the waveguide, one upstream, the other downstream.) Each of transducers 360, 362, 364 and 366 may alternate as an exciter or receiver. The transducers are instrumented in a manner so that circulation Γ of the vortices shed from the sensor section 332, i.e., the shedder, can be measured. As circulation Γ changes sign in response to the alternating shedding at the Strouhal frequency, the transit time measured clockwise versus counterclockwise increases or decreases from a mean value <t>. Circulation can be determined from a measurement of the time for the ultrasound beams 356a and 356b to pass in a clockwise direction from transducer 360 to transducer 362 and from transducer 364 to transducer 366, respectively, and in the opposite counterclockwise direction. Ideally, the clockwise and counterclockwise time measurements are made over a closed path in the fluid. However, if the two path segments connecting the fluid paths already mentioned but immediately adjacent the pipe wall are so close to the wall, there is essentially no flow along them. This means the difference between clockwise and counterclockwise interrogations of those connecting paths is negligibly small. The distance along the centerline of the flow path between the waveguide sensor section 332 and the beam path between transducers 364 and 366 should not allow space for an even number of vortices. That is, only one vortex should lie between the waveguide sensor and the beam path 356(b) between transducers 364 and 366. Less than two complete vortices will be present in the circulation sensing path if the downstream path is located within two diameters of the waveguide sensor section 330. Generally speaking, according to the compactness objective of this invention, and in order that the axial extent of the piping over which one must exercise control is not excessive, and furthermore, to guarantee that fluid conditions are substantially constant over the entire axial length of the fluid specimen being sensed, a useful guideline is that the mass flowrate sensing is accomplished within an overall axial length of approximately five pipe diameters or less. The transit time of the two beams 356a and 356b when operated sequentially and alternately clockwise and counterclockwise provides a measurement of the change in sign of the circulation. The frequency of this changing sign of circulation is proportional to velocity. That is, if the fluid passing between the beams includes an eddy having clockwise rotation and the ultrasound beams can switch between clockwise and counterclockwise interrogations faster than the passage of that eddy, the difference in transit time for the clockwise and counterclockwise interrogations can be measured. By alternately reversing the ultrasonic beam directions, the transit time through the fluid in counterclockwise and clockwise senses is measured while a particular vortex is enclosed between the beams. With the vortices shedding alternately off the top and bottom of the bluff body of the waveguide sensor, the circulation $\Gamma$ of the fluid is measured and the frequency of change in sign of the circulation is proportional to velocity. This method affords a measurement of the vortex shedding frequency using high frequency ultrasonic interrogation beams which can be as high as several MHz for liquids and perhaps 0.5 MHz for gases, which frequencies are high enough so that the measurements of the change in sign of circulation are essentially immune to noise and other interference. It also enables an optimization of the shape of the waveguide sensor section 332 for optimizing the density measurement by the torsional waveguide, i.e. using a diamond-shaped cross section, while enabling velocity measurement as a function of the shedding frequency of the shed vortices. The clockwise and counterclockwise interrogations can be made as suggested by contrapropagation timing methods known in the art. They can also be accomplished using singaround methods. Again, as it is only necessary to derive the frequency of the change in sign, it is sufficient to interrogate in one direction only, i.e. clockwise or counterclockwise, rather than both directions. Unidirectional interrogation is not expected to yield an accurate measure of circulation but it only needs to yield the frequency of the change in sign of circulation. A further simplification interrogates the circulation effect over but one path, not two.

As can be readily ascertained from the foregoing, the mass flow rate sensor hereof provides an integral unit which may be safely installed and removed in existing pipe lines. When installed, the sensor is minimally invasive without causing any substantial pressure drop. The sensor is useful in both turbulent and laminar flows and applicable to single phase, two phase, and multiphase fluids. Moreover, the transducers may be located on one side of the sensor when access to opposite sides of the pipe line is awkward or not accessible.

Figure 12:
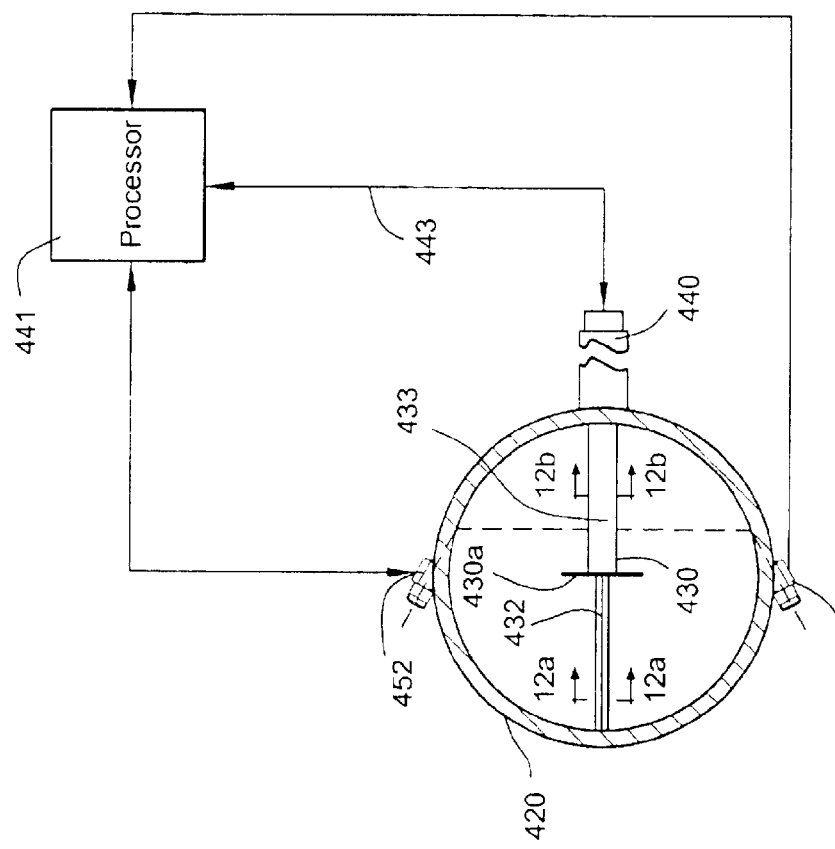
FIG. 12 is a schematic axial illustration of another form of a sensor with associated electronics.
Figure 12A:
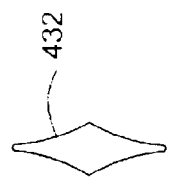
FIGS. 12*a* and 12*b* are cross sectional view of the waveguide of FIG. 12 taken about on lines 12*a*—12*a* and 12*b*—12*b*, respectively, of FIG. 12.
Figure 12B:
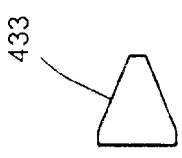

Referring now to FIGS. 12, 12a and 12b, there is illustrated in FIG. 12 an axial cross section of a flow path wherein like reference numerals are applied to like parts as in the prior embodiments preceded by the reference numeral 4. In this axial cross sectional view of the flow path, the wafer 420 mounts a waveguide 430 of two different cross sections spaced axially from one another along the waveguide. The waveguide 430 includes for example a diamond shaped cross sectional configuration 432 (FIG. 12a) and a bluff body polygonal cross sectional shape 433, for example as illustrated in FIG. 12b. A thin disk 430a of diameter slightly larger than the width of the bluff portion of shedding segment 433 is optionally placed at the intersection of the two cross sections to separate shedding phenomena from the two segments. The diamond shaped cross sectional configuration 432 of the waveguide 430 as noted previously provides optimum accurate results for determination of density. The cross sectional configuration 433 has been used previously to accurately determine velocity based on vortex shedding frequency. By locating the transducer 440 at one end of the waveguide 430 and using electronic processing, e.g. as illustrated in FIG. 3, velocity and density signals may be obtained similarly as in FIGS. 2 and 3. Alternatively, and instead of determining both velocity and density parameters using the single waveguide with the different cross sectional configurations, a system similar to that illustrated in FIGS. 6 and 7 may be used. For example, the transducer 440 may provide a signal 443 from the transducer 440 containing intervals related uniquely to density to a processor 441. Transducers 452 and 454, externally mounted as shown, are utilized to transmit an electronic beam downstream of the waveguide 430 and particularly downstream of the portion of waveguide 430 shaped to optimally provide the velocity parameter, i.e. the shape illustrated in FIG. 12b. Transducer 452 excites a beam which passes through the vortices shed from the body 433 and the signal is received by transducer 454 for transmission to the processor 441. The signals received by processor 441 are processed similarly as described and illustrated herein, e.g. with respect to FIG. 7, to obtain the mass flow rate. Since the vortex shedding frequency is proportional to flow velocity but inversely proportional to the width of the strut, by using a "composite" shedder with two different strut sections, the system can generate at a given flow, two frequencies that bear a fixed and predetermined relationship to one another. This fact may be utilized in extracting the shedding frequencies when ambient noise is large.

Figure 13:
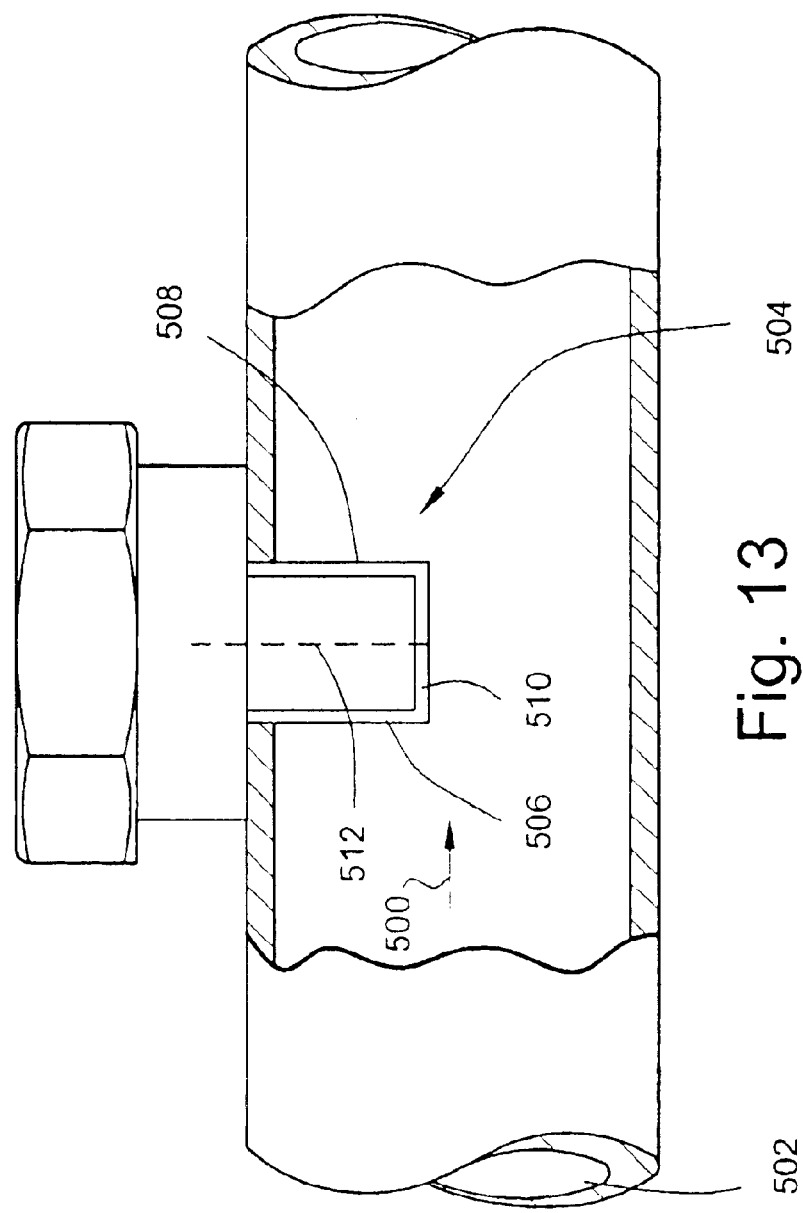
FIG. 13 and FIG. 13*a* are schematic illustrations of further forms of a sensor according to a further aspect of the present invention.
Figure 13A:
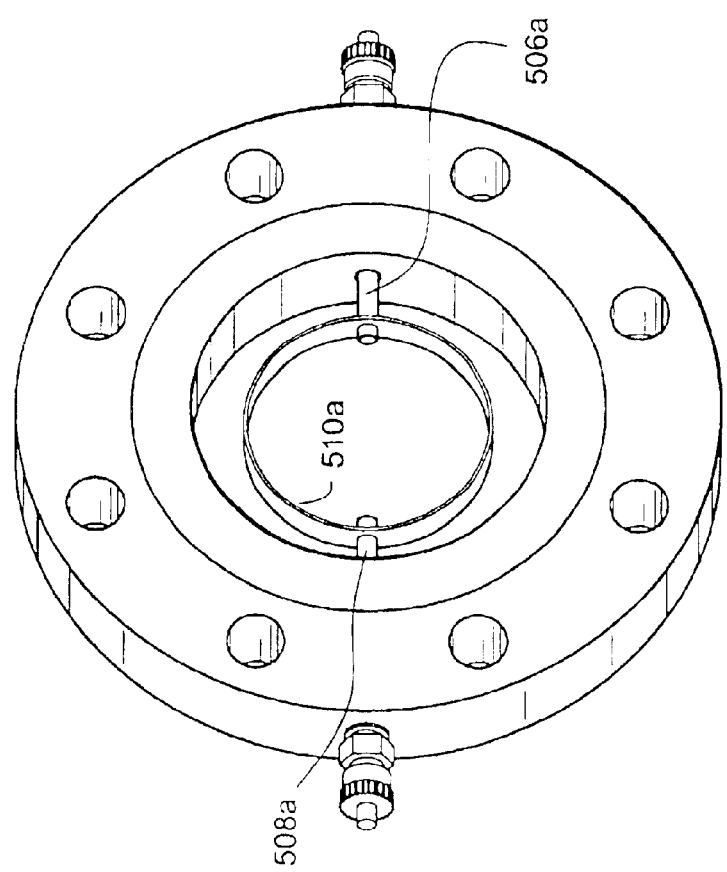

Referring now to FIGS. 13, 13a and 14, there is illustrated a further embodiment of the present invention. In FIG. 13, there is illustrated a flow path 500 defined by a pipe 502. In this embodiment, a mass flow rate meter includes a generally U-shaped waveguide assemblage generally designated 504. Assemblage 504 includes a generally U-shaped sensor having a pair of legs 506 and 508 axially spaced one from the other and connected to one another at distal ends by a base 510. The legs 506 and 508 comprise vortex shedder segments with bluff faces disposed in opposite directions such that the sensor can be used to detect mass flow rate for bi-directional flows. In the illustrated example, the upstream vortex shedder 506 sheds vortices which appear between the legs 506 and 508. An ultrasonic beam 512 is passed from an exciter, not shown, through the vortices and reflected by the base 510 of the sensor to a receiver, also not shown. Thus the beam encounters vortices downstream of the upstream vortex shedder 506 causing a modulation of the phase and/or amplitude of the signal received by the receiver and which modulated frequency within the modulated signal is proportional to the vortex shedding frequency. By electronically processing that vortex shedding frequency, a velocity parameter may be obtained. In FIG. 13a the base is formed in the shape of a ring 510a. Flexural waves are launched in the ring by mode conversion from an incoming extensional wave incident orthogonally on one side by a first leg 506a. At a diametrically opposite point on the ring, which is the density-responsive element, the flexural waves are reconverted back to extensional and proceed as extensional along second leg 508a. These two legs and optionally others support the ring to withstand fluid flow forces and also convey reaction forces caused by vortex shedding to receiving transducer(s) not shown. The ring may have a diameter approximately 75% of the inside diameter of the pipe, wafer body or flange in which it is mounted. The ring should be centralized so all portions of it are exposed to substantially the same fluid flow velocity. The ring's cross section favors shedding, yet also yields a guided flexural wave speed responsive to density.

To obtain the density parameter necessary to a determination of mass flow rate, in a U-shaped sensor of the type illustrated it is advantageous to utilize, rather than a torsional wave, a flexural wave, preferably the lowest-order flexural wave, whose speed decreases depending on the density of the adjacent fluid. The advantage of flexure over torsion stems from the ease of generating in this configuration a density-responsive guided wave using an orthogonally-incident extensional wave. For this purpose, an extensional wave is progagated by a transducer (exciter), not shown, along the upstream leg 506 to the base 510. The extensional wave, through a mode conversion process, excites the base 510 in a flexural mode (schematically illustrated in FIG. 14 by the dashed lines 514). The flexural mode responds to density. The response is not necessarily linear over wide ranges in density. However, the response can be calibrated by a method similar to that shown in FIGS. 21a–e or by immersion in liquids of known density. Temperature compensation can be obtained by pulse-echo timing of the extensional wave in leg 506 or leg 508. The pulse-echo timing of extensional waves in the legs, after dividing by two, yields the extensional time in each leg. In turn, subtracting the travel time in each leg from the total through-transmission transit time, yields the flexural contribution from that portion of the ultrasonic path in the base 510. The flexural mode of base 510 mode converts to an extensional wave in the downstream leg 508 transmitted to a receiver, not shown. By measuring the total time the waves propagate along the upstream leg 506, base 510 and downstream leg 508 and subtracting out the time of propagation along the upstream and downstream legs 506 and 508, respectively, the transit time across the length of the base 510 is ascertained and can be related to density. Consequently, the density and velocity signals may be processed to obtain the mass flow rate.

Referring now to FIGS. 15 and 16, it will be appreciated that as the diameter of the waveguide increases, the waveguide becomes more dispersive to one or more modes. For a given wave length, waveguide material and waveguide cross sectional dimension and shape, the waveguide should be compact, e.g., short, and not over 12 inches. A compact waveguide lessens the problems of dispersion. It will also be appreciated that the diameter of many of the transducers available to introduce torsional and extensional waves exceed the diameter of the desired waveguide. For example, for a waveguide having a diameter of 0.375 inches, it is necessary to couple four transducers at 90° intervals such that one pair of transducers provides a stress couple in a torsional direction and the other pair provides an extensional wave while using transducer cases of almost twice the diameter of the waveguide, e.g., 0.687 inches. In short, because the waveguide diameter is less than the transducer diameter, the four transducers cannot be coupled all at once at the end of the waveguide.

Referring to FIG. 15, a buffer 600 is added to the wafer 602 to couple each of the transducer end faces 604 to the waveguide 606. That is, a buffer 600 of a diameter intermediate the diameter of the waveguide 606 and the case of the transducer 608 and of a length so that it can be installed within one quadrant of a six port clamp body is illustrated, four ports in the respective four quadrants (FIG. 15) and two ports at axial ends thereof. The buffer 600 is stepped and may be bonded or clamped to the radiating face of the associated transducer 608 or may be pressure coupled thereto. The electrical connections for the transducers may be exposed through the end face of the wafer 602, i.e., the rear face of the clamp. Thus, the electronics module may be attached immediately to the end face 610 of the clamp opposite the waveguide 606.

If impedance matching is utilized as in FIG. 16, it may comprise tapered flats that make a small angle of a few degrees with each of the flat faces of the diamond segment 602. FIG. 16 shows two tapers 612. Torsional impedance is transformed, i.e., reduced, by two effects: a slowing and a reduction in the polar moment of inertia. It will be recalled that torsional impedance in the waveguide depends on the waveguide density times torsional sound speed times the polar moment of inertia. This means the tapers are more effective per unit length in transforming torsional impedance than conical sections as used in prior art. Torsional speed is constant along a straight conical waveguide. While this might be viewed as a disadvantage for impedance matching, it can be an advantage when the segment intended to measure temperature with torsional waves includes one or even two conical portions as in FIG. 1g.

As implied in FIG. 15 or FIG. 16 (or FIG. 1d), the security screw (not shown, but which may be as small as a number 0–80 or M3.5 metric socket head screw) locks the waveguide into its recess when tightened into the waveguide's tapped security hub. If the hub is non-circular, the locking action resists push, pull and twist. The head of the screw fits into recess 602a of FIG. 15 and also in FIG. 16. In FIG. 15, the shape of that recess 602a is diamond and corresponds in a visually accessible region of the clamp to the remote orientation of diamond segment 602. This enables an observer to verify the orientation of the density sensor within an opaque pipe. A preferred locked position is where the interface between the waveguide and the hub lies at the centerline of the clamp and hence is contacted by half the radiating face of the transducer or its buffer extension. The shear transducer in this configuration is typically a commercially available transducer of nominal frequency 2.25 MHz. When the waveguide is thus contacted, the waveguide appears to or in effect filters out high frequency energy via a dispersion or cut-off mechanism and the observed echoes lie within a downshifted frequency band on the order of 50–200 kHz. In effect, the system operates in the lowest order mode, which for torsion in a circular cross section elastic waveguide, means non-dispersive propagation, and little or no dispersion in the noncircular portion. Lowest order modes also apply to flexural waves. By operating at a sufficiently low frequency, flexural phase velocity can be kept small, even smaller than the longitudinal velocity in the adjacent fluid. As a consequence there is no radiation of sound into the fluid. As noted previously, torsional and flexural guided waves share this property of avoiding energy loss by radiation into the adjacent fluid. The details of how each wave avoids radiating are different, however. Extensional or longitudinal waves in a rod usually radiate some energy into the adjacent fluid because (a) the speed in the rod usually is faster than in the fluid, and (b) the extensional or longitudinal waves are able to weakly couple to longitudinal waves in the fluid.

Figure 17A:
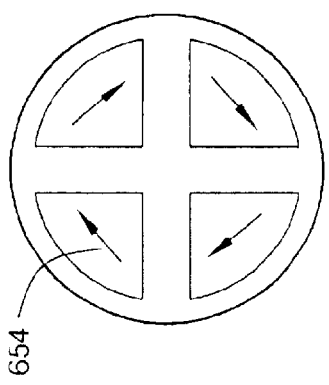
FIGS. 17*a*–17*d* illustrate various forms of mounting drivers on the end of a torsional waveguide to excite the waveguide in a torsional mode.
Figure 17B:
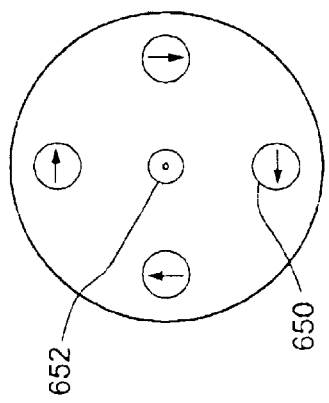
Figure 17C:
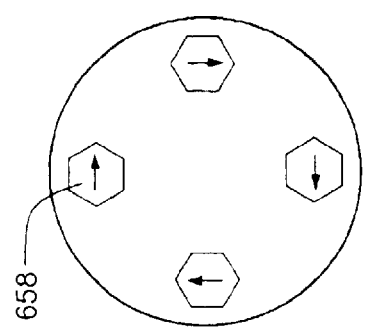
Figure 17D:
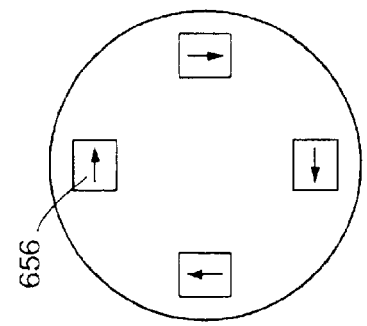

Referring now to FIGS. 17a–17d, there are illustrated various arrays of piezoelectric crystals bonded to a waveguide. For example, in FIG. 17a, thickness-shear piezoelectric crystals 650 are arranged tangentially in quadrants about the axis of the waveguide to introduce torsional effects. The waveguide upon removal of the excitating impulse on the crystals relaxes and returns elastically to a nominal position. In FIG. 17a, the central piezoelectric crystal 652 vibrates to provide an extensional wave. In FIG. 17b, piezoelectric crystals 654 are provided in quadrants separated by cuts in the end of the waveguide. Various other shapes of the crystals 656 and 658 are illustrated in FIGS. 17c and 17d.

Figure 18:
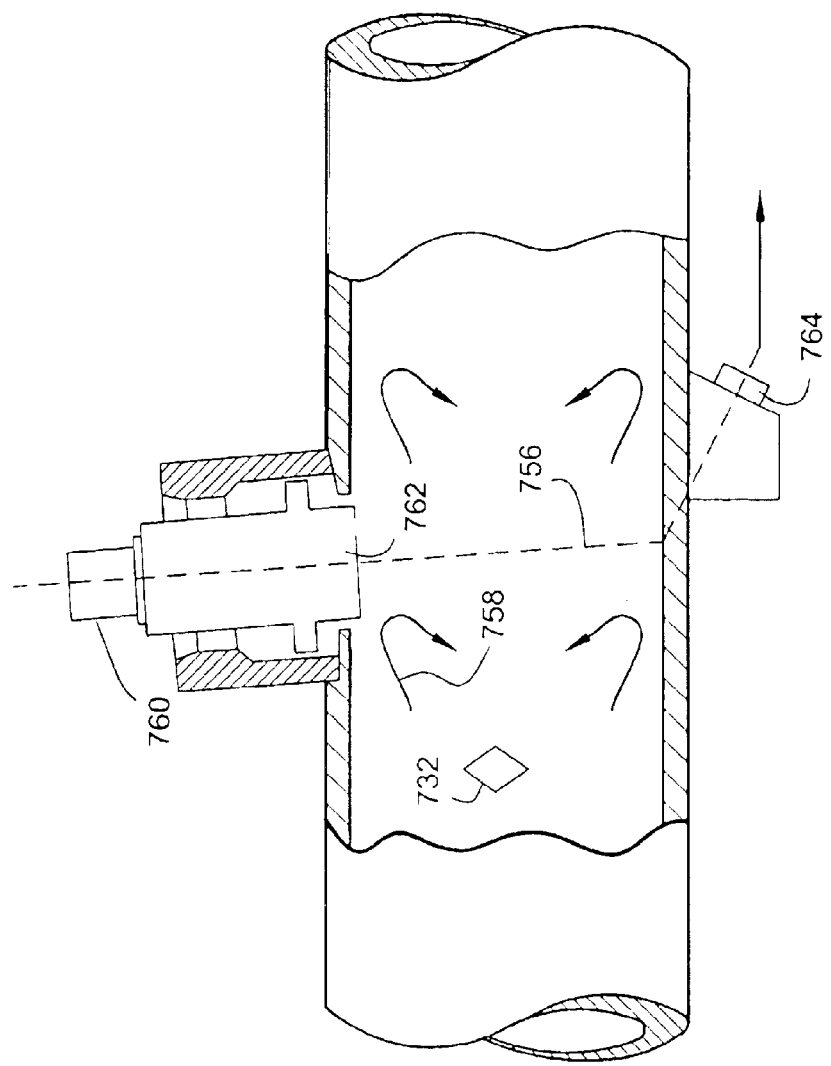
FIG. 18 is a schematic illustration of wetted and non-wetted transducers for effecting the velocity measurement.

Referring now to FIG. 18, there is illustrated an embodiment similar to that of FIGS. 6 and 7 wherein the density parameter is determined by an ultrasonic mass loading frequency response of the waveguide 732 and the velocity parameter is determined by an ultrasonic beam 756 traversing the vortices 758 shed from the waveguide. In this embodiment however, only one transducer 760 has a wetted surface 762 exposed to the fluid flowing within the pipe. The opposite transducer 764 is angled and secured outside of the pipe, i.e., an external clamp-on transducer. This arrangement affords a way of measuring vortex shedding with only one transducer in contact with the fluid hence requiring only one opening in the pipe through which the fluid flows. The second transducer 764 is external to the pipe and angled to take advantage of the higher energy transmission as the ultrasonic beam impacts the pipe.

Consideration is here given to the material forming the elastic waveguides, including the sensor sections, e.g. 32, in the preceding embodiments. Compared to the transit time in vacuum or air, the sensor section would yield an increase in torsional transit time when immersed in a liquid such as water in inverse proportion to the waveguide's density. For a given shape, e.g. diamond, the increase in sensitivity to fluid density as a function of sensor material, is thus, in order of increasing sensitivity, stainless steel, titanium, aluminum. Therefore, for a given cross sectional shape, aluminum is much more sensitive than titanium, and titanium is more sensitive than stainless steel. Aluminum, however, while suitable for some liquids and gases, is not sufficiently corrosion resistant to operate in many industrial liquids. Another way to achieve increased sensitivity for a given elastic waveguide, and at the same time impart other useful characteristics like corrosion resistance or fouling-resistance, is to coat it with plastic (e.g. polyetrafluoroethylene, or "Teflon") having a lower density than the elastic part (elastic core). This construction provides a composite with an average density lower than the elastic core alone. The entire waveguide, or at least the entire cross section of the density-sensing section can be made of a suitable plastic. For the portion made entirely of plastic, that plastic should have a high allowable operating temperature. This generally implies that among plastics, it will have a relatively small temperature coefficient of sound speed, and be not too attenuating to ultrasonic waves. Plastics offer economy in manufacturing. One such high-temperature plastic material is Ultem 1000 manufactured by the General Electric Company. Another is Vespel made by DuPont. Other anticorrosion measures include nickel plating and anodizing.

Figure 20:
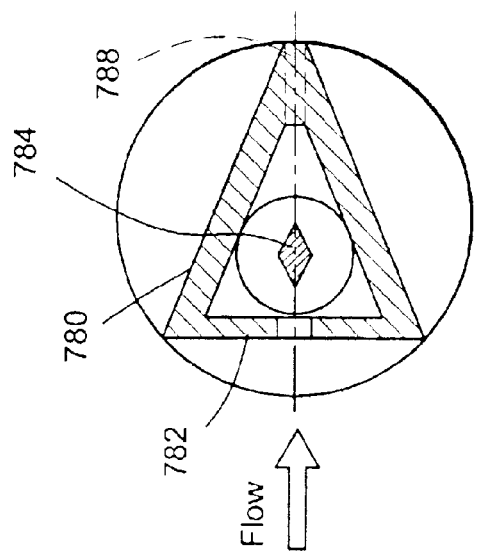
FIG. 20 is a cross sectional view thereof taken about on line 20—20 in FIG. 19.
Figure 19:
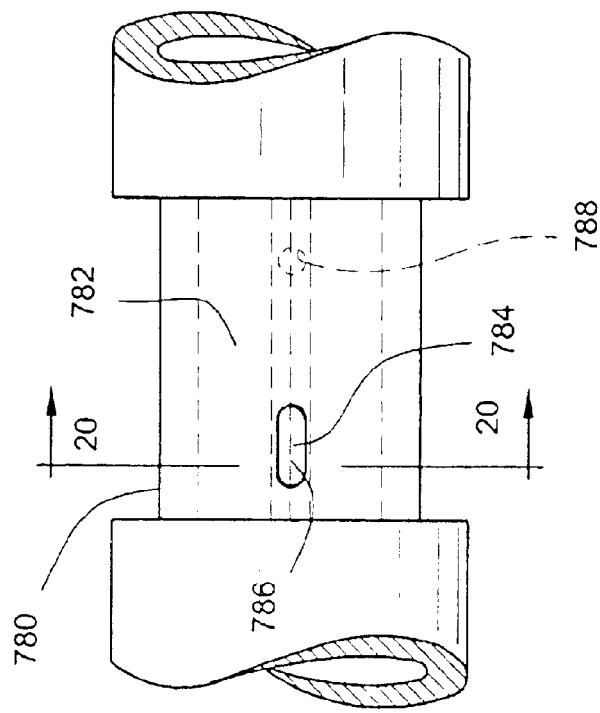
FIG. 19 is a schematic illustration of a functionally separated densitometer and a vortex shedder in a single probe.

Referring now to FIGS. 19 and 20, a sheath 780 may be internally threaded at one end to thread onto the hub portion of a clamp. While the sheath 780 may be shaped as a cylindrical structure, the sheath may have a cross section with a flat bluff leading face 782 (FIG. 20) or a shape corresponding to other known shedders that shed vortices in a manner more reliable than a circular tube. However, by using the densitometer's sheath as the shedder, rather than the densitometer section 784 itself, there is provided a way of further separating the vortex shedding function from the density sensing function while utilizing a single probe. The sheath's cross sectional dimensions can be substantially larger than the density sensor, by a factor of 2 to 10, which may be preferred for use in pipes of large diameter and/or pipes in which the flow velocity is high. Vortices shed by the sheath 780 can be detected by piezoelectric transducers within the clamp or by piezoelectric transducers placed downstream and which interrogate the wake, as described previously. In this construction, wherein the sheath becomes the shedder, the density sensor section preferably is centralized within the sheath, protected from most of the force of a high-speed fluid flow impact. The sheath 780 contains one or more inlet slots or holes 786 and exit slots or holes 788 to allow and encourage a small but adequate flow of fluid to pass around the sensor section 784 and exit into the flow path. The fluid therefore surrounds segment 784 with a representative fluid density that is refreshed as new fluid enters the sheath at not more than a moderate flow rate. The slots or holes 786 and 788 are placed near or in line with the pipe's axis and as far as practical from the regions of the sheath 780 that are regions of vortex separation. Appropriate regions for the inlet slots or holes are the stagnation region on the sheath's leading face (which is preferably a bluff face), and for the outlet slots 180 degrees downstream. The inlet and outlet slots are preferably slightly axially offset from one another relative to the waveguide 784. For example, when the sheath is installed across the pipe, the passageways in the sheath may be located such that the inlet slot lies near the middle of the pipe and the outlet passages lie near the walls of the pipe, to refresh and clean the density sensor with representative fluid yet limit the flow rate within the sheath 780. The vortices are shed elsewhere, e.g. not adjacent the slots or holes 786 or 788 but near the top and bottom portions of the sheath. Thus, the waveguide densitometer 784, and its concentric sheath 780 serving as a velocity responsive vortex shedder, constitutes a parallel or coaxial combination of elements in a single probe, in contrast to the series combinations illustrated, e.g. in FIGS. 6–7. When the mass flowmeter probe assembly consists of a perforated vortex shedding sheath generally surrounding the density sensor as just described, it is obvious that both segments of the mass flowmeter are subjected to substantially the same average fluid composition, density, temperature and pressure. The "concentric" sheath and density sensor are much closer than one pipe diameter. However, in constructions where the sources of the density and flow information are not congruent, i.e. not in the same element (e.g. FIG. 2) but instead involve two segments, one needs to place both segments close enough in terms of pipe diameter so fluid density and velocity parameters involved in the mass flowrate computation are nearly the same and preferably identical at both segments and over the axial extent of the measurements. Five pipe diameters is herein recommended as a guide for the overall axial extent.

Referring now to FIGS. 21a–21e, several arrangements are shown for calibrating or verifying density sensor performance using argon, air and helium, respectively. In FIG. 21a the pipe 800, initially full of ordinary air, is open ended and oriented with open end up to be filled with a gas denser than air, such as argon. As argon is poured slowly into the pipe, the sound speed measured across the path between exciter and receiver transducers 802 within the pipe cross 804 at the open end registers a gradually decreasing sound speed as the path is filled initially with air [of MW (molecular weight)=29] but gradually with a mixture richer in argon, and eventually essentially pure argon (MW=40). The intervalometer 806 in FIG. 21e makes the necessary sound speed measurements in the test gas as well as in the density sensor also disposed within the pipe 800 as illustrated (and for each of the other calibration tests illustrated in FIGS. 21b–21d). At 20 deg C. the sound speed is well known in argon, air and helium, e.g. 319 m/s, 343 m/s and 1000 m/s, respectively. By monitoring the sound speed of the test gas one readily determines when equilibrium has been achieved. The corresponding density of the gas to which the density sensor is exposed is now known from the sound speed measurement and the density measurement from the waveguide e.g. 30 are compared for calibration purposes. The horizontal pipe of FIG. 21b containing the sensor and transducers, (not shown in this Figure) is open to atmospheric air and similar comparisons are made for calibration purposes. The inverted pipe 810 shown in FIG. 21c may be similarly filled with a gas, such as helium that floats upward, displacing air or argon. The MW of helium is 4 and has a sound speed essentially the square root of ten or 3.16 times faster than argon, and a density $\frac{1}{10}$ of argon's. Comparisons of the sound speed and waveguide sensed densities are similarly made for calibration purposes. The pressurized vessel 812 in FIG. 21d is pressurized with air e.g. at ten bar and then safely allowed to blowdown to atmospheric pressure, thereby surrounding the density sensor within it to a reproducible thermal transient. The pipe cross 804 and gas sound speed sensing transducers 802 shown in FIG. 21a can be assumed present in these other pipe configurations, and are not shown explicitly. In the past, calibration of density sensors required using liquids of varying density such as salt solutions, or water at slightly different temperature. The use of air or inert gases of different density, where the gas density at atmospheric pressure is recognized as being in the range of 0.1% of the density of typical liquids, provides an easy way to calibrate and verify density sensor performance in gases, where the intended use is typically in liquid. Air's density may be taken as 1.29 kg/m$^3$ while water's is 998 kg/m$^3$, for example. Since the chamber in FIG. 21d can be operated at slightly reduced pressure (as well as at elevated pressure) the density of air may be brought down to exactly 0.1% of water's density. It will be appreciated that using a pressurized gas as suggested in FIG. 12d, in order to calibrate at densities closer to those expected in liquid density-sensing applications, the gas inside the calibration vessel can be argon or other gas denser than air. Provided suitable safety precautions are adhered to, and in particular, paying attention to the need to secure the waveguide against being driven out of the pressure vessel, one can use pressures substantially higher than 10 bar. As a numerical example, and to convey the idea simply and without including the gas compressibility factor Z, suppose the gas is argon at ordinary temperature but at 100 bar. The argon gas density is now approximately 180 kg/m^3. This is much higher than the densities of the suggested gases near atmospheric pressure, and is recognized as being some 20 to 25% of the densities of common liquids. If this method is used, it will be useful to measure gas temperature and pressure and include Z as part of determining the reference density. Monitoring the gas sound speed across the pipe cross (if present) will be useful to monitor the approach to equilibrium in the gas environment. It is unlikely, if the end objective is sensing densities of liquids, that this calibration method would be used at gas pressures much over 200 atmospheres, or approximately 3000 psig. However, if the objective is to measure gas densities, then calibration in a pressurized gas may be a useful way to demonstrate sensor and system performance.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended.

What is claimed is:

1. Apparatus for determining mass flow rate of a fluid in a flow passage having a predetermined area, comprising
    a sensor including a waveguide disposed in the flow passage and having a section exposed to the fluid flowing in the passage;
    means in the flow path for shedding vortices;
    an exciter for propagating an ultrasonic wave along said waveguide including along said section and having a propagation velocity dependent upon the density of the fluid adjacent said section;
    first means coupled to said waveguide for detecting the propagated wave and providing a first output signal proportional to the transit time of the propagated wave along the density-responsive section of the waveguide for determining the density of the fluid;
    second means forming part of said sensor for detecting the shedding frequency of the vortices shed from said vortex shedding means and providing a second output signal proportional thereto for determining the velocity of the fluid; and
    a processor for generating an indication of the mass flow rate of the fluid through the passage based on the first and second signals and the predetermined area of the flow passage.

2. Apparatus according to claim 1 wherein said first means detects density-responsive signals of the propagated wave at a frequency greater than the shedding frequencies.

3. Apparatus sensor according to claim 2 wherein said detected density-responsive signals are at a frequency of 20 kHz or more and the shedding frequencies are 10 kHz or less.

4. Apparatus according to claim 3 wherein said vortex shedding means includes said waveguide section, said second means being coupled to said waveguide for sensing torque in said waveguide in response to vortices shed from the waveguide section.

5. Apparatus according to claim 1 wherein said vortex shedding means includes a sheath surrounding said waveguide section.

6. Apparatus according to claim 5 wherein said sheath has a first aperture for receiving density representative portions of said fluid for flow about said waveguide section and a second aperture for flowing fluid from within the sheath into the flow stream.

7. Apparatus according to claim 1 wherein said second means includes a transducer for directing an acoustical beam through vortices downstream of the waveguide and a receiver for detecting modulation of the phase or amplitude of the acoustical beam and providing said second output signal proportional to the shedding frequency of the vortices for determining the velocity of the fluid.

8. Apparatus according to claim 1 wherein said second means includes a transducer on one side of the flow passage for transmitting an ultrasonic beam, a reflector on an opposite side of the flow passage for reflecting the beam and a receiver for detecting modulation of the phase or amplitude of the reflected beam, said beam including a first beam portion from said transducer to said reflector lying upstream of the waveguide and a second beam portion from the reflector to the second receiver and passing through the shed vortices to provide a second output signal proportional to the shedding frequency of the vortices for determining the velocity of the fluid.

9. Apparatus according to claim 1 wherein said second means includes means for measuring the change in sign of the circulation of the shed vortices to provide said second output signal proportional to the velocity of the fluid.

10. Apparatus according to claim 1 wherein said exciter propagates ultrasonic waves along one segment of the waveguide section in flexure, said first means detecting signals that include a flexural wave contribution, and means for separating said contribution from the total transit time, and providing said first output signal to determine the fluid density.

11. Apparatus according to claim 10 wherein said vortex shedding means includes two bluff shapes facing in opposite axial directions to shed vortices for bidirectional flow.

12. Apparatus according to claim 1 wherein said exciter propagates ultrasonic waves along the waveguide section in flexure, said first means detecting the flexural wave and providing said first output signal to determine the fluid density wherein said flexural waves have major frequency components in the inaudible ultrasonic band above 20 kHz and below 200 kHz.

13. Apparatus according to claim 1 wherein said shedding frequency lies between about 100 Hz and 10 kHz, said exciter propagating torsional waves along said waveguide section in an inaudible frequency band at least ten times higher in frequency than said shedding frequency.

14. Apparatus according to claim 1 wherein the fluid flow passage comprises an axially extending pipe, said sensor including a wafer body installed in said pipe and having an axial length not in excess of about five times the nominal pipe size and up to about three times the internal diameter of said wafer body.

15. Apparatus according to claim 1 wherein said fluid flow passage comprises an axial extending pipe and said waveguide extends across the pipe occupying 10% or less of the flow area of the pipe.

16. Apparatus according to claim 1 wherein said vortex shedding means includes said waveguide section, said second means being coupled to said waveguide for sensing torque in said waveguide in response to vortices shed from the waveguide section, said second means including a transducer for directing an acoustical beam through vortices downstream of said waveguide and a receiver for detecting modulation of the phase or amplitude of the acoustical beam to provide an additional output signal proportional to the frequency of the shed vortices for determining the velocity of the fluid, the second output signal and the additional output signal serving as a cross-check on the accuracy of the velocity determination.

17. Apparatus according to claim 1 wherein said waveguide includes at least one impedance transformation utilizing two or more tapers disposed symmetrically about the axis of the waveguide.

18. Apparatus according to claim 1 wherein said ultrasonic wave does not substantially couple to acoustic noise in the fluid.

19. A method for determining mass flow rate of a fluid in a flow passage having a predetermined area, comprising the steps of:
  providing a waveguide disposed in the flow passage with a section exposed to the fluid flowing in the passage;
  providing a vortex shedder in the flow path for shedding vortices;
  propagating an ultrasonic wave along said waveguide including along said section having a propagation velocity dependent upon the density of the fluid adjacent said section;
  detecting the propagated wave;
  providing a first output signal proportional to the transit time of the detected propagated wave along the density-responsive section of the waveguide for determining the density of the fluid;
  detecting the frequency of the vortices shed from said vortex shedder;
  providing a second output signal proportional to the detected shedding frequency for determining the velocity of the fluid; and
  generating an indication of the mass flow rate of the fluid through the passage based on the first and second signals and the predetermined area of the flow passage.

20. A method according to claim 19 including detecting density-responsive signals of the propagated wave at a frequency greater than the shedding frequencies.

21. A method according to claim 20 including detecting the density-responsive signals at a frequency of 20 kHz or more and detecting shedding frequencies of 10 kHz or less.

22. A method according to claim 19 including propagating torsional waves along said waveguide section and sensing torque in said waveguide in response to vortices shed from the waveguide section.

23. A method according to claim 19 including providing a sheath surrounding said waveguide section for shedding the vortices.

24. A method according to claim 23 including providing a first aperture in said sheath for receiving density representative portions of said fluid for flow about said waveguide section and providing a second aperture in said sheath for flowing fluid from within the sheath into the flow stream.

25. A method according to claim 19 including directing an acoustical beam through vortices downstream of the waveguide, detecting a modulation of the phase or amplitude of the acoustical beam and providing said second output signal proportional to the shedding frequency of the vortices for determining the velocity of the fluid.

26. A method according to claim 19 including transmitting an ultrasonic beam across the flow passage upstream of the waveguide, reflecting the beam across the flow passage downstream of the waveguide through the vortices to a receiver, and detecting a modulation of the phase or amplitude of the reflected beam.

27. A method according to claim 19 including measuring a change in sign of the circulation of the shed vortices to provide said second output signal proportional to the velocity of the fluid.

28. A method according to claim 19 including propagating ultrasonic waves along the waveguide section in flexure, detecting the flexural waves and providing said first output signal in response to said detection to determine the fluid density.

29. A method according to claim 19 including propagating an ultrasonic wave of the lower order along said waveguide.

30. A method according to claim 19 including propagating an ultrasonic wave which does not radiate compressional waves to any significance into the fluid adjacent said waveguide.

* * * * *